(12) United States Patent
Hollister et al.

(10) Patent No.: US 10,639,175 B2
(45) Date of Patent: *May 5, 2020

(54) POROUS BIDIRECTIONAL BELLOWED TRACHEAL RECONSTRUCTION DEVICE

(71) Applicant: THE REGENTS OF THE UNIVERSITY OF MICHIGAN, Ann Arbor, MI (US)

(72) Inventors: Scott J. Hollister, Saline, MI (US); Glenn E. Green, Dexter, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 413 days.

This patent is subject to a terminal disclaimer.

(21) Appl. No.: 14/929,555

(22) Filed: Nov. 2, 2015

(65) Prior Publication Data

US 2016/0051385 A1 Feb. 25, 2016

Related U.S. Application Data

(63) Continuation of application No. 13/715,715, filed on Dec. 14, 2012, now Pat. No. 9,180,029.

(Continued)

(51) Int. Cl.
*A61F 2/94* (2013.01)
*A61F 2/848* (2013.01)
(Continued)

(52) U.S. Cl.
CPC ............... *A61F 2/848* (2013.01); *A61F 2/94* (2013.01); *A61L 31/005* (2013.01); *A61L 31/06* (2013.01);
(Continued)

(58) Field of Classification Search
CPC ............... A61F 2/848; A61F 2002/043; A61F 2002/046; A61F 2002/044;
(Continued)

(56) References Cited

U.S. PATENT DOCUMENTS 5,258,027 A * 11/1993 Berghaus .................. A61F 2/04
623/9
6,001,117 A * 12/1999 Huxel ....................... A61F 2/04
606/191

(Continued)

OTHER PUBLICATIONS

Boogaard, Ruben, et al, "Tracheomalacia and Bronchomalacia in Children: Incidence and Patient Characteristics," Chest Journal, vol. 128, No. 5, pp. 3391-3397 (Nov. 2005).

(Continued)

*Primary Examiner* — Suba Ganesan
*Assistant Examiner* — Aren Patel
(74) *Attorney, Agent, or Firm* — Harness, Dickey & Pierce, P.L.C.

(57) ABSTRACT

Implantable splinting devices for supporting a passageway defect in a patient that is formed from one or more support structures including a polymer or a polymer and acellularized tissue matrix that define a structural component that substantially conforms to a defective passageway of the patient. The structural component also has a plurality of pores. The implantable splinting device is capable of being placed around a trachea, a bronchi, an esophagus and a blood vessel of a patient. The implantable splinting device may also be configured for placement between the trachea, and the esophagus of a patient.

22 Claims, 17 Drawing Sheets

Related U.S. Application Data

(60) Provisional application No. 61/570,568, filed on Dec. 14, 2011.

(51) Int. Cl.

| | |
|---|---|
| A61L 31/00 | (2006.01) |
| A61L 31/06 | (2006.01) |
| A61L 31/14 | (2006.01) |
| A61L 31/16 | (2006.01) |
| B29C 64/153 | (2017.01) |
| A61F 2/04 | (2013.01) |
| B33Y 10/00 | (2015.01) |
| B33Y 80/00 | (2015.01) |
| B29K 67/00 | (2006.01) |
| B29K 105/00 | (2006.01) |
| B29L 31/00 | (2006.01) |

(52) U.S. Cl.
CPC ............. *A61L 31/148* (2013.01); *A61L 31/16* (2013.01); *B29C 64/153* (2017.08); *A61F 2002/043* (2013.01); *A61F 2002/044* (2013.01); *A61F 2002/046* (2013.01); *A61F 2220/0008* (2013.01); *A61F 2220/0075* (2013.01); *A61F 2220/0091* (2013.01); *B29K 2067/00* (2013.01); *B29K 2105/251* (2013.01); *B29K 2995/0056* (2013.01); *B29L 2031/7534* (2013.01); *B33Y 10/00* (2014.12); *B33Y 80/00* (2014.12)

(58) Field of Classification Search
CPC .... A61F 2002/048; A61F 2/94; B29C 64/153; A61L 31/16; A61L 31/06; A61L 31/148; A61L 31/005
See application file for complete search history.

(56) References Cited

U.S. PATENT DOCUMENTS

| | | | |
|---|---|---|---|
| 6,080,177 | A | 6/2000 | Igaki et al. |
| 7,087,200 | B2 | 8/2006 | Taboas et al. |
| 7,174,282 | B2 | 2/2007 | Hollister et al. |
| 7,509,240 | B2 | 3/2009 | Das et al. |
| 9,180,029 | B2 | 11/2015 | Hollister et al. |
| 2003/0028255 | A1* | 2/2003 | Hartig ............... A61F 2/04 623/23.7 |
| 2004/0210300 | A1* | 10/2004 | Aboul-Hosn ............ A61F 2/07 623/1.23 |
| 2008/0195198 | A1 | 8/2008 | Asgari |
| 2009/0043371 | A1* | 2/2009 | Fearnot ................ A61F 2/07 623/1.13 |
| 2011/0230974 | A1 | 9/2011 | Musani |
| 2012/0035715 | A1* | 2/2012 | Robida .................. A61F 2/848 623/1.36 |

OTHER PUBLICATIONS

Bugmann, Philippe, et al., "Extratracheal Biodegradable Splint to Treat Life-Threatening Tracheomalacia," Ann. Thorac. Surg., vol. 78, pp. 1446-1448 (2004).
Chappell, Bill, "3-D Printer Makes Life-Saving Splint for Baby Boy's Airway," National Public Radio, The Two-Way Blog, available at <http://www.npr.org/blogs/thetwo-way/2013/05/23/186273900/3-d-printer-makes-life-saving-splint-for-baby-boys-airway> (May 23, 2013) (2 pages).
Edine, Nicole, "3-D Printers Are Saving Babies' Lives One Breath at a Time," The Huffington Post, available at <http://www.huffingtonpost.com/2014/03/21/3d-printer-health_n_4993565.html> (Mar. 21, 2014) (4 pages).

Filler, Robert M., et al., "Treatment of Segmental Tracheomalacia and Bronchomalacia by Implantation of an Airway Splint," Journal of Pediatric Surgery, vol. 17, No. 5, pp. 597-603 (Oct. 1982).
FoxNews.com, "Doctors use 3D-printed device to help baby breathe on his own," Fox News, available at <http://www.foxnews.com/health/2014/03/18/doctors-use-3d-printed-device-to-help-baby-breathe-on-his-own/> (Mar. 18, 2014) (1 page).
Kucera, Kristin A., et al., "Tracheal Replacements: Part 1," ASAIO Journal, vol. 53, No. 4, pp. 497-505 (2007).
Marchione, Marilynn, "Doctors save Ohio boy by 'printing' an airway tube: A medical first: Doctors save Ohio boy by laser-printing an airway tube so he can breathe," Associated Press, available at <http://news.yahoo.com/doctors-save-ohio-boy-printing-125228957.html> (May 23, 2013) (2 pages).
Masson, Mary, "Second baby's life saved with 3D printed airway splints," University of Michigan, Michigan Engineering, available at <http://www.engin.umich.edu/college/about/news/stories/2014/march/second-baby-s-life-saved-with-3d-printed-airway-splints> (Mar. 14, 2014) (3 pages).
Miller, Rina, "U-M doctors use 3-D printer to build life-saving device," Michigan Radio, available at <http://michiganradio.org/post/u-m-doctors-use-3-d-printer-build-life-saving-device> (May 22, 2013) (3 pages).
Robey, Thomas C., et al., "Biodegradable External Tracheal Stents and Their Use in a Rabbit Tracheal Reconstruction Model," The Laryngoscope, vol. 110, pp. 1936-1942 (Nov. 2000).
Sewall, Gregory K., et al., "Comparison of resorbable poly-L-lactic acid-polyglycolic acid and internal palmaz stents for the surgical correction of severe tracheomalacia," The Annals of Otology, Rhinology & Laryngology, vol. 112, No. 6, pp. 515-521 (Jun. 2003).
Smith, Stephanie, "3-D printer helps save dying baby," CNN.com, available at <http://www.cnn.com/2013/05/22/health/baby-surgery/index.html?hpt=hp_c4> (May 23, 2013) (5 pages).
Stein, Rob, "Doctors Use 3-D Printing to Help a Baby Breathe," National Public Radio, Shots: Health News From NPR, available at <http://www.npr.org/blogs/health/2014/03/17/289042381/doctors-use-3-d-printing-to-help-a-baby-breathe> (Mar. 17, 2014) (4 pages).
Vondrys, David, et al., "First Experience With Biodegradable Airway Stents in Children," Ann. Thorac. Surg., vol. 92, pp. 1870-1874 (2011).
Wilson, Jacque, et al., "3-D printer saves toddler struggling to breathe," CNN, available at <http://www.cnn.com/2014/03/18/health/3d-printer-michigan-baby/> (Mar. 28, 2014) (2 pages).
Wilson, J. F., "Mechanics of Bellows: A Critical Survey," Int. J. Mech. Sci., vol. 26, No. 11/12, pp. 593-605 (1984).
Zhang, Huina, et al., "Chemically-Conjugated Bone Morphogenetic Protein-2 on Three-Dimensional Polycaprolactone Scaffolds Stimulates Osteogenic Activity in Bone Marrow Stromal Cells," Tissue Engineering: Part A, vol. 16, No. 11, pp. 3441-3448 (2010) (published online Jul. 16, 2010).
Zhang, Huina, et al., "Comparison of Bone Marrow Stromal Cell Behaviors on Poly(caprolactone) with or without Surface Modification: Studies on Cell Adhesion, Survival and Proliferation," Journal of Biomaterials Science, vol. 20, pp. 1975-1993 (2009).
Zhang, Huina, et al., "The interaction between bone marrow stromal cells and RGD-modified three-dimensional porous polycaprolactone scaffolds," Biomaterials, vol. 30, pp. 4063-4069 (2009) (published online May 31, 2009).
Cho, Jong Ho, et al., "External Tracheal Stabilzation Technique for Acquired Tracheomalacia using a Tailored Silicone Tube," The Annals of Thoracic Surgery, vol. 94, pp. 1356-1358 (2012).
Hagl, Siegfried, et al., "External Stabilization of Long-Segment Tracheobronchomalacia Guided by Intraoperative Bronchoscopy," The Annals of Thoracic Surgery, vol. 64, pp. 1412-1421 (1997).
Ley, Sebastian, et al., "Long-Term Outcome After External Tracheal Stabilization Due to Congenital Tracheal Instability" The Annals of Thoracic Surgery, vol. 89, pp. 918-925 (2010).
Sakamoto, T., et al., "One-stage intracardiac repair in combination with external stenting of the trachea and right bronchus for tetralogy of Fallot with an absent pulmonary valve and tracheobronchomalacia" The Journal of Thoracic and Cardiovascular Surgery. vol. 130(6), pp. 1717-1718 (2005).

(56) References Cited

OTHER PUBLICATIONS

Takazawa, S., et al. External Stabilization for severe tracheobronchomalacia using separated ring-reinforced ePTFE grafts is effective and safe on a long-term basis. Pediatric Surgery International. vol. 29. pp. 1165-1169 (2013).

* cited by examiner

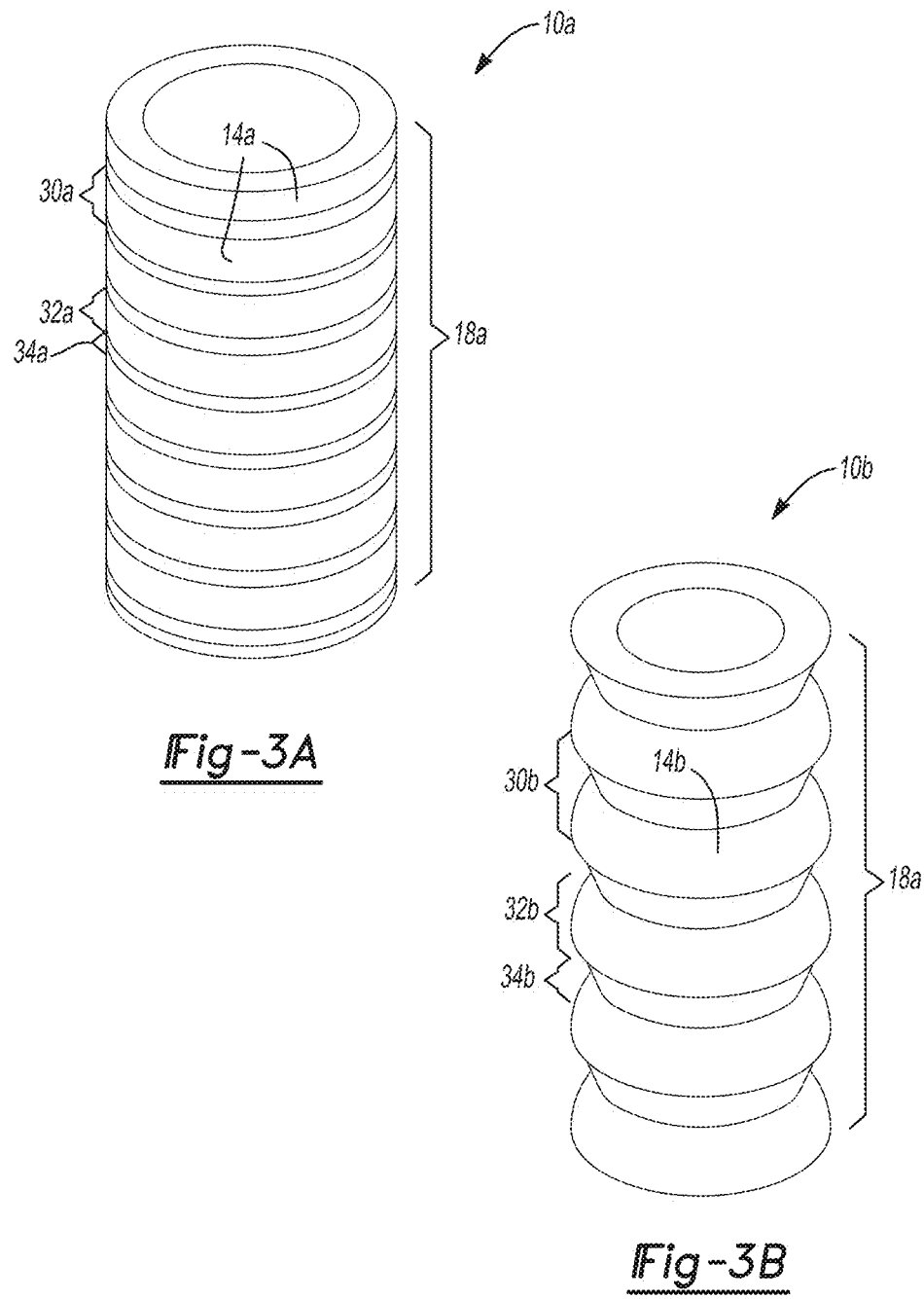

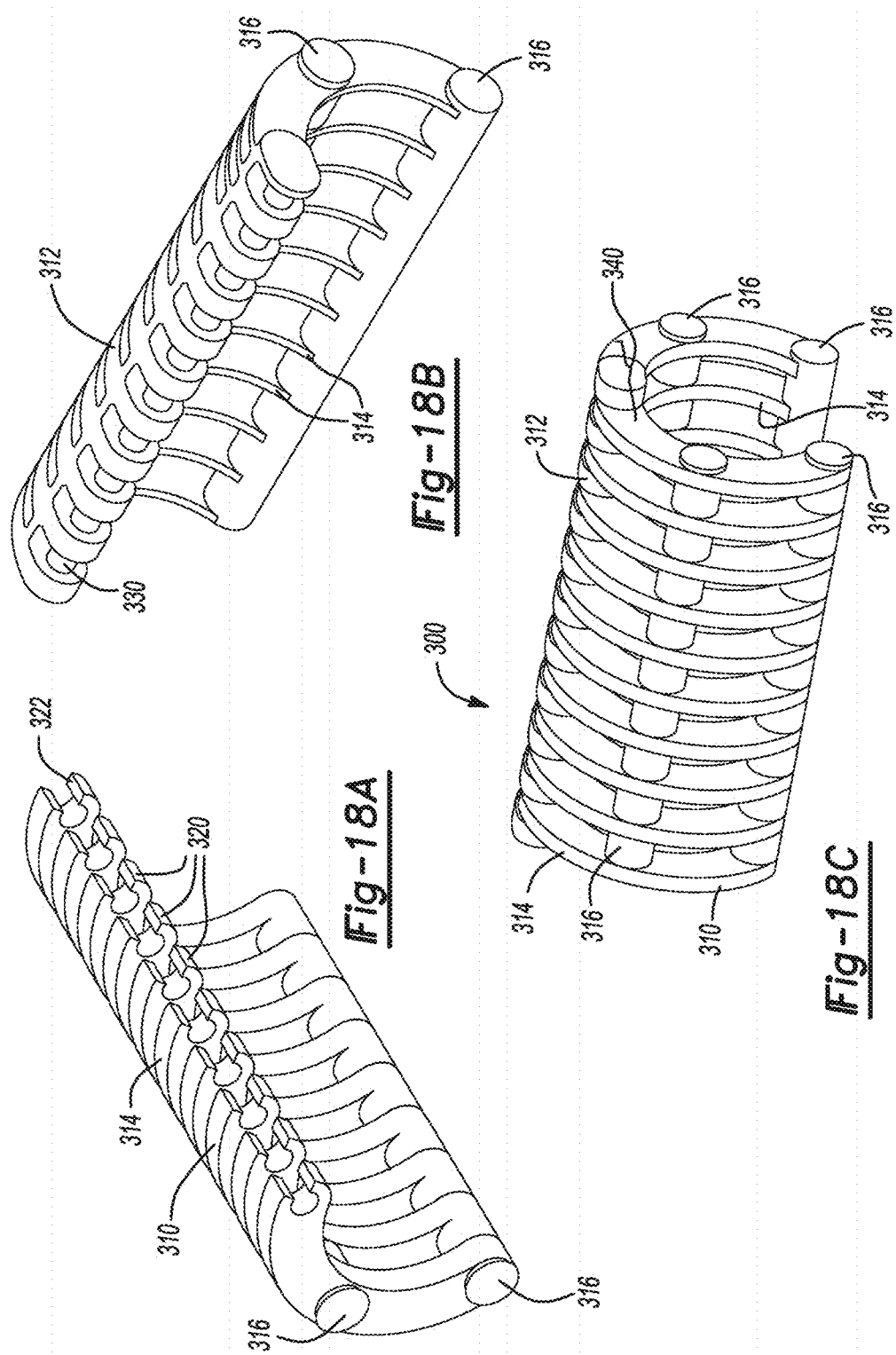

POROUS BIDIRECTIONAL BELLOWED TRACHEAL RECONSTRUCTION DEVICE

CROSS-REFERENCE TO RELATED APPLICATIONS

This application is a continuation of U.S. patent application Ser. No. 13/715,715, filed on Dec. 14, 2012, which claims the benefit of U.S. Provisional Application No. 61/570,568, filed on Dec. 14, 2011. The entire disclosures of each of the above applications are incorporated herein by reference.

GOVERNMENT RIGHTS

This invention was made with government support under RR024986 awarded by the National Institutes of Health. The government has certain rights in the invention.

FIELD

The present disclosure relates to highly customizable, implantable splinting devices for supporting defects in passageways, such as airways, of a patient having a defect in the passageway.

BACKGROUND

The present technology relates to materials and implants useful in maintaining patency in a passageway, such as an airway, and treating conditions where a passageway in a human or other animal subject has collapsed or weakened like in tracheomalacia or a tracheoesophageal fistula. Tracheomalacia or tracheobronchomalacia (TBM) are congenital or acquired deficiencies of tracheal and/or bronchial cartilages. These conditions may be characterized by flaccidity of the supporting tracheal or bronchial cartilage, resulting in airway obstruction, respiratory difficulties and, in severe cases, death. It is estimated that this condition affects about 1 in 2,100 children, TBM presents with respiratory difficulties, chronic cough, wheezing, recurrent infections, and in severe cases, acute life-threatening events. In adults and infants who have severe forms of TBM that are unresponsive to medical management or have life-threatening symptoms, surgical intervention may be necessary. Severe cases can result in death or require tracheostomy with ventilation for 2-3 years, a burden on the child and family. Current treatment techniques often include mechanical ventilation, implantation of tracheal stents and surgery. For example, as noted in the Cochrane reviews, outcomes of all surgical/mechanical interventions to date have been widely associated with failure, morbidity and mortality.

Surgical/mechanical devices for addressing TBM can be broadly categorized into stents, namely devices placed inside or within the passageway (e.g., trachea), and splints, namely devices implanted externally around the passageway (e.g., the trachea). Stents offer an easier surgical approach, but are associated with more complications, including stent migration, granulation tissue leading to secondary obstruction, the need for multiple procedures and even death. Further, conventional silicone and metal tracheal stents have posed difficulties in placement, stent migration or distortion, lack of tissue growth, permanence and decreased adjustability. These complications have prompted the U.S. Food and Drug Administration (FDA) to issue a warning against the use of tracheal stents.

Splints, however, have also exhibited various complications, including tracheal erosion and granuloma formation. These detrimental effects are believed to be attributable to the conventional materials used to form the splints in that they are too stiff. Further, there is concern that overly stiff devices restrict tracheobronchial growth, causing more long term complications, especially in children. Tracheal banding in rat models has been found not only to restrict tracheal growth, but to lead to smaller overall lung volumes, less alveoli and smaller overall body growth. However, devices that are not stiff enough fail to create/maintain tracheobronchial patency and, further, easily migrate from the desired position. While degradable devices have been proposed as a partial solution, these devices have been observed to degrade too rapidly, thus allowing insufficient time for the trachea to remodel and become structurally competent, thereby failing to resolve the TBM or other passageway defects. Thus, implantable devices that improve upon these issues to decrease mortality, improve patient outcomes, including improve growth to permit the defective passageway to develop structural competency, and to enhance the quality of life of an animal having such a passageway defect would be desirable.

SUMMARY

This section provides a general summary of the disclosure and is not a comprehensive disclosure of its full scope or all of its features.

In various embodiments, the present technology provides an implantable splinting device for supporting a passageway defect in a human patient or other animal comprising a polymer. The implantable splinting device comprises one or more support structures, which together may define a structural component, and a plurality of pores. The implantable splinting device is capable of being placed around at least a portion of a passageway of a patient selected from the group consisting of: a trachea, a bronchi, an esophagus and a blood vessel. The implantable splinting device may also be configured for placement between the trachea and the esophagus of a patient, in certain variations.

In other variations, an implantable splinting device for supporting a defect in a passageway of a human or animal subject comprises one or more support structures together defining a structural component that substantially conforms to at least a portion of the passageway. The one or more support structures comprise a biocompatible, biomedically acceptable polymeric material. Further, the one or more support structures may optionally comprise a longitudinal opening formed within the one or more support structures to facilitate placement of the implantable splinting device over the passageway. The implantable splinting device comprises a plurality of apertures defined in at least a portion of the one or more support structures, which are capable of receiving a suture for attaching the implantable splinting device to at least a portion of the passageway.

In other aspects, the present technology provides an implantable splinting device for supporting a defect in a passageway of a human or other animal subject that comprises one or more support structures together defining a body or structural component that substantially conforms to at least a portion of the passageway. The implantable device comprises a plurality of apertures defined in at least a portion of the one or more support structures. The one or more support structures comprise a biocompatible or biomedically acceptable polymeric material, so that the body or structural component is capable of restricting displacement to less than 10% under a direct compression load of about 50N, while permitting outward radial displacement of at least 100% of an initial diameter of the body or structural component under non-stress conditions under a radial pressure of about 50N. Such an implantable splinting device may thus provide adequate structural support for the passageway so as to withstand compression forces and torsion experienced in vivo, while permitting flexibility that allows growth and revascularization of tissue of the passageway.

In yet other aspects, the present technology provides methods of making an implantable splinting device for application to a defect in a passageway of a human or other animal patient that comprises forming a biocompatible or biomedically acceptable polymeric material into a U-shaped structural component comprising a plurality of apertures and a plurality of bellows, wherein the U-shaped structural component substantially conforms to at least a portion of the passageway selected from the group consisting of a trachea, a bronchi, an esophagus and a blood vessel. In certain aspects, the implantable splinting device is designed from a set of medical image data specific to the human or animal patient. In this way, the implantable splinting device is highly customized for a particular human or animal.

In other variations, a method of making an implantable splinting device for application to a passageway defect in a human or other animal patient is provided. The method comprises designing a structural component for the implantable splinting device from a set of medical image data of the passageway defect specific to the patient. Then, a biodegradable polymer is laser sintered to form the structural component. Lastly, a plurality of pores is integrated within the structure capable of receiving a suture for attaching the implantable splinting device to at least a portion of the passageway.

In other aspects, the present technology provides an implantable splinting device for supporting a trachealesophageal fistula in a human or animal patient comprising a polymer. The implantable splinting device may comprise a tracheal U-shaped structural component and an esophageal U-shaped structural component. The structural components may be formed from a series of support structures and comprise a plurality of apertures. In other aspects, the implantable splinting device may comprise a first component and a second component. In certain variations, the first component and the second component are joined together by a hinge.

The present technology additionally provides a method of making an implantable splinting device for application to a passageway defect in a human or animal patient comprising: providing a polymer, forming the polymer into a U-shaped structural component by forming a series of support structures, and integrating a plurality of pores within the series of support structures.

An advantageous feature of the present technology is a unique implantable splinting device that can be designed from the standard diameters and lengths of the trachea, bronchi, esophagus and blood vessels or customarily designed from the patient's specific medical image data prior to surgery.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 3A-3B show a square wave bellow (3A) and a triangle wave bellow (3B) of an implantable splinting device according to certain aspects of the present teachings.

Figure 13A:
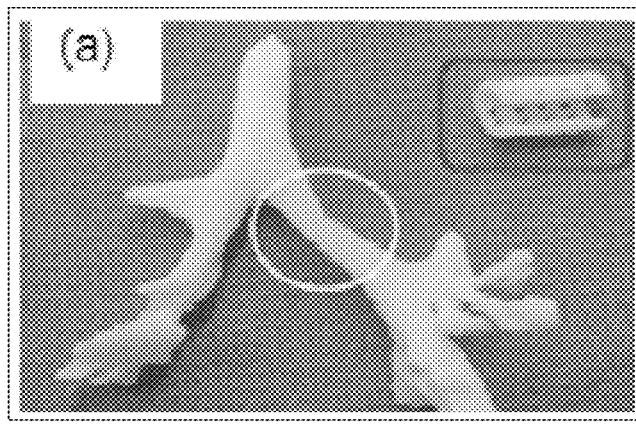
Figure 13B:
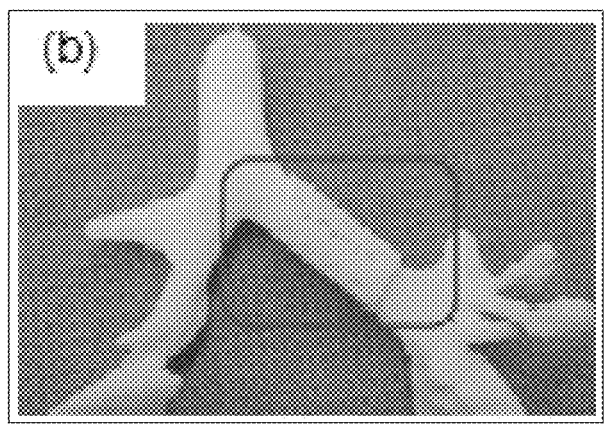
Figure 13C:
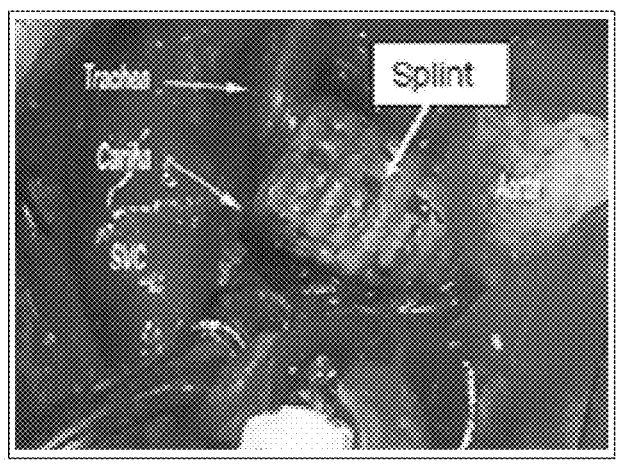

FIGS. 13A-13C show models and surgical techniques of an implantable splinting device used for treating a tracheobronchomalacia condition in a human subject according to certain aspects of the present technology. FIG. 13A shows a model of a trachea and bronchi from a patient, where a defective malacic segment is circled and the implantable splinting device comprising polycaprolactone is shown in the inset, while FIG. 13B shows the implantable splinting device applied to the bronchus of the model to support the malacic segment. FIG. 13C shows surgical implantation of the implantable splinting device in a three-month old human patient. The splinting device is placed around the left bronchus, which is then sutured into the implantable splinting device to open the obstructed bronchus.

Figure 14A:
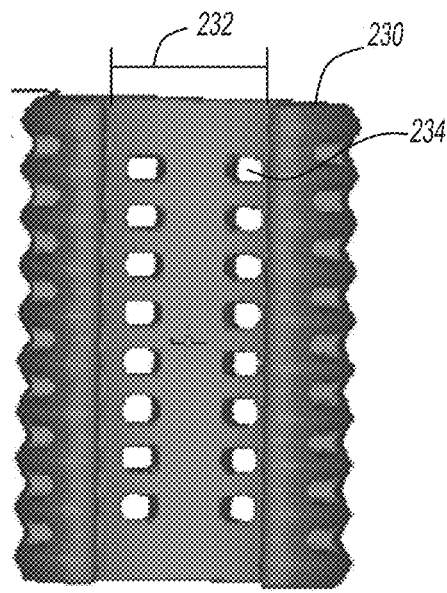
Figure 14B:
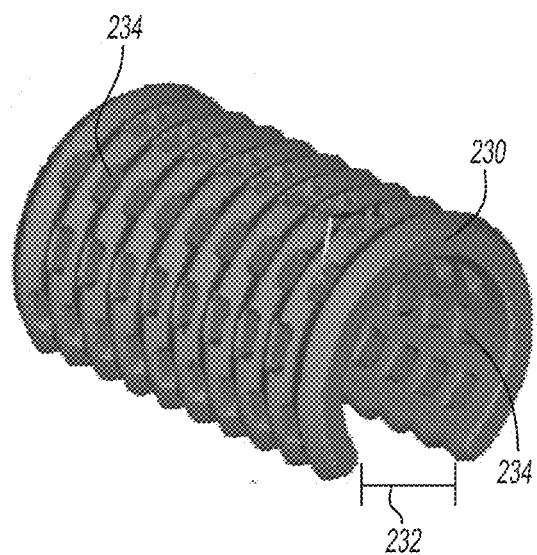
Figure 14C:
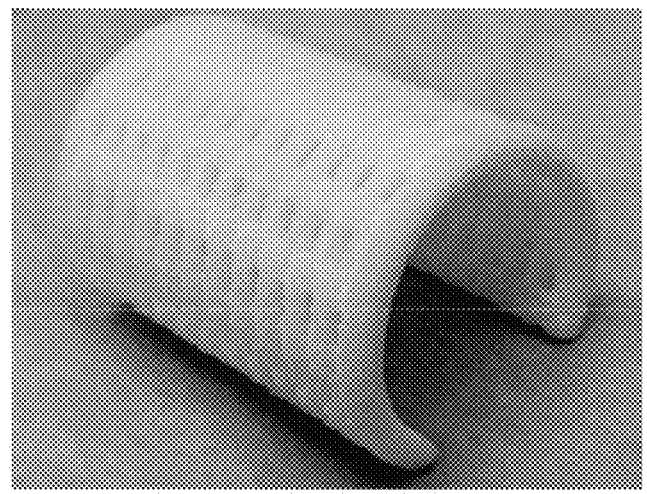

FIGS. 14A-14C show an implantable splinting device according to certain aspects of the present teachings used in a porcine model. FIGS. 14A and 14B respectively show a posterior view and an oblique view of the implantable splinting device, including a plurality of openings or apertures for suture needle hole placement. FIG. 14C shows a laser sintered polycaprolactone implantable splinting device formed from the designs of FIGS. 14A and 14B.

Figure 15A:
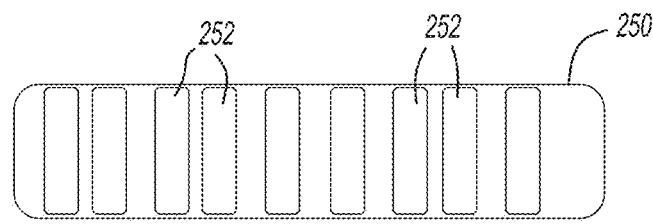
Figure 15B:
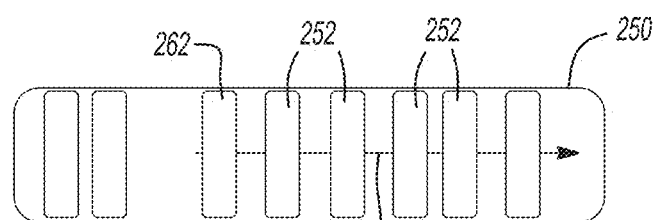
Figure 15C:
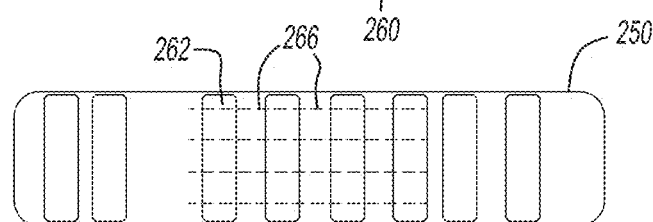
Figure 15D:
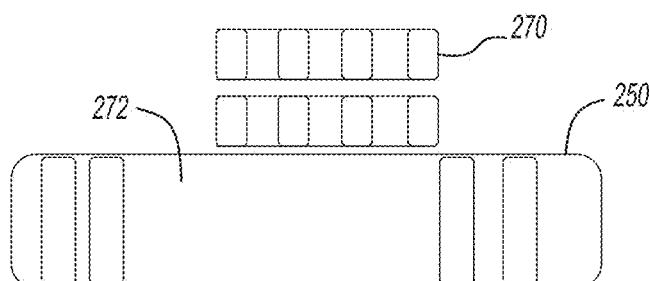
Figure 15E:
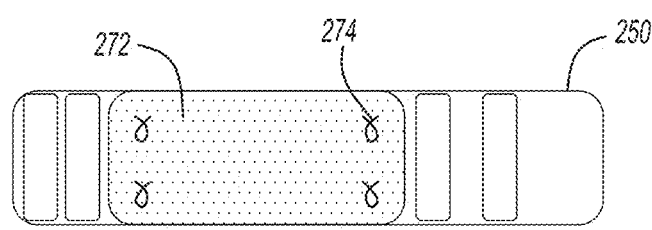

FIGS. 15A-15E show illustrations of surgical creation of tracheomalacia in a porcine model. More specifically, a detailed illustration of surgical development of severe tracheomalacia in control animals and placement in experimental animals of an implantable splinting device according to certain aspects of the present technology. FIG. 15A shows exposure of a trachea of a pig. FIG. 15B shows subperichondrial dissociation of internal tracheal mucosa of the pig. FIG. 15C shows a division of overlying tracheal cartilaginous rings in the pig. FIG. 15D depicts inferiorly based tracheal cartilage with intervening outer mucosa of the pig. FIG. 15E shows the implantable splinting device overlying the trachea of the pig sutured in place.

Figure 16A:
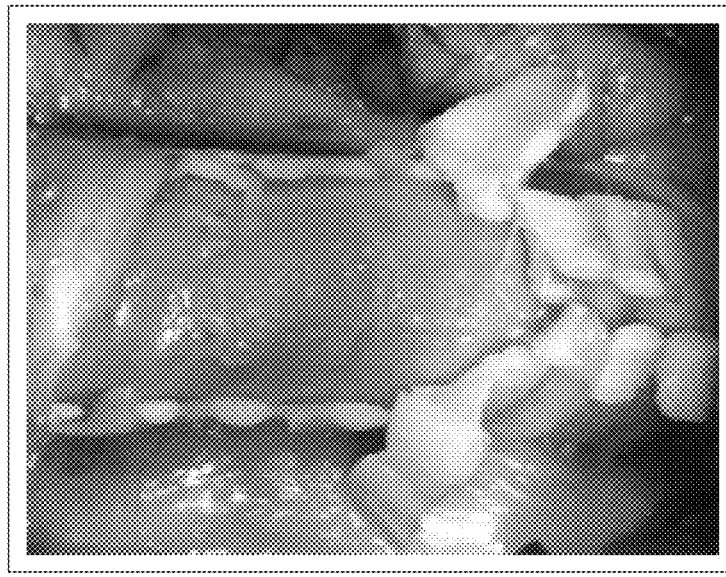
Figure 16B:
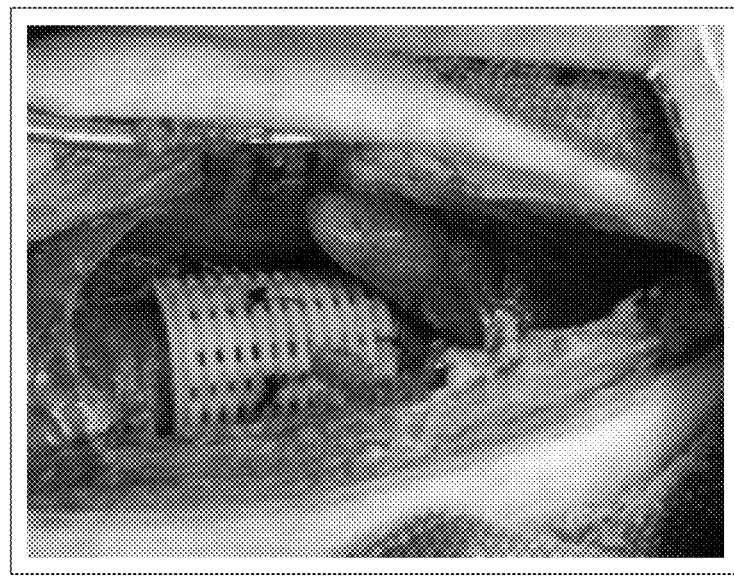

FIGS. 16A-16B show intraoperative photographs of a severe tracheomalacia model illustrated in FIGS. 15A-15D, while FIG. 16B shows the implantable splinting device overlying the trachea of the pig sutured in place, as illustrated in FIG. 15E.

Figure 17:
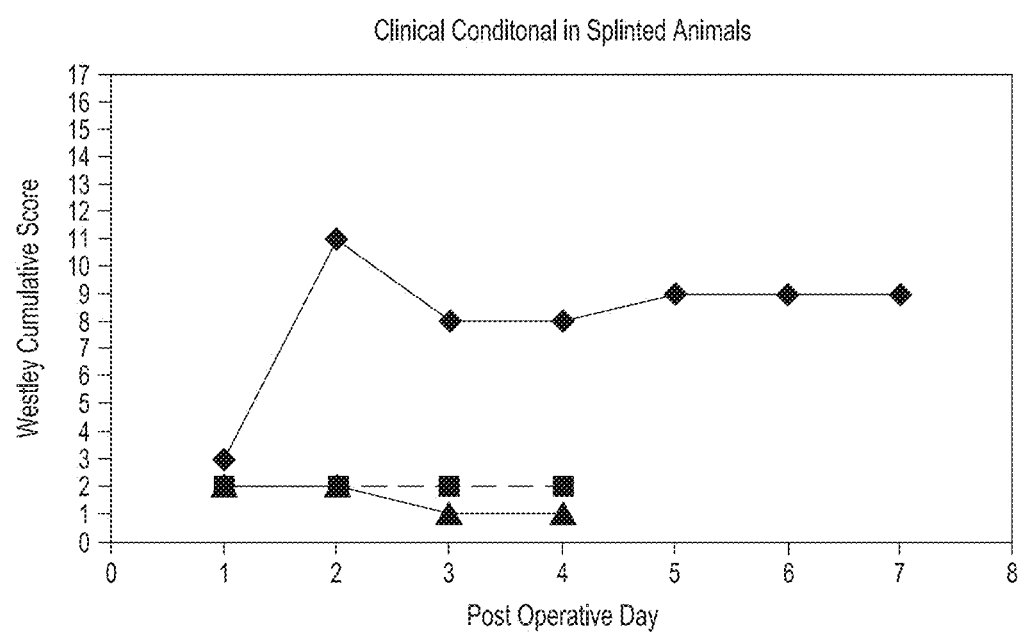

FIG. 17 shows post-operative cumulative clinical scores of the porcine model based on the Westley Clinical Croup scale.

FIGS. 18A-18C show another implantable splinting device embodiment according to certain aspects of the present technology, which comprises a first component and a second distinct component, which are joined together via a hinge structure.

Corresponding reference numerals indicate corresponding parts throughout the several views of the drawings.

DETAILED DESCRIPTION

The following description of technology is merely exemplary in nature of the composition, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The disclosure of all patents and patent applications cited in this disclosure are incorporated by reference herein.

As used herein, the words "prefer" or "preferable" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

In various aspects, the present teachings provide an implantable device for an animal (human or other animals) that serves as a splint around at least a portion of an exterior of a lumen or passageway, which is particularly advantageous for use with passageways exhibiting a physical defect or weakened structure. Passageways include lumens or physical structures within an organism that in a healthy condition permit fluid to flow therethrough, such as air, carbon dioxide, blood, plasma, and the like. Thus, the implantable splinting device of certain aspects of the present technology may be used for treatment of conditions where a passageway in a human or other animal subject has collapsed, is damaged, or is otherwise weakened. The implantable splinting device according to certain aspects of the present teachings can serve to separate and support such a passageway from a source of actual or potential external compression. It may also support a passageway that collapses or potentially collapses in its normal environment. The implantable splinting device may also separate a passageway that has not actually collapsed, but is weakened or has a potential risk of collapse. Accordingly, specific materials to be used in the splinting device of the present technology are preferably biomedically acceptable. Such a "biomedically acceptable" material is one that is suitable for use with humans and/or animals without undue adverse side effects (such as toxicity, irritation, and allergic response) commensurate with a reasonable benefit/risk ratio.

In certain aspects, the implantable splinting device may be used for the treatment of passageway defects in humans or other animal subjects, including mammalian animals, such as livestock, horses, cats, dogs, and the like. As used herein, the term "subject" or "patient" includes humans or animals, unless otherwise specified. In various embodiments, the implantable splinting device is capable of being placed around at least a portion of a passageway within the subject. In certain variations, the implantable splinting device may fully surround the circumference of a passageway, while in other variations, the implantable splinting device may only support a portion of the circumference of the passageway. As noted above, such a passageway within the subject in a healthy condition permits fluid communication and in certain variations, may be selected from the group consisting of: a trachea, a bronchi, an esophagus, a blood vessel, and combinations thereof. Typically, an implantable splinting device is suitable for use in a subject that exhibits one or more passageway defects. "Passageway defects" include any condition involving tissue of the passageway that is inadequate, weakened or obstructed for physiological or cosmetic purposes. Such passageway defects include those that are congenital, those that result from or are symptomatic of disease or trauma, and those that are consequent to surgical or other medical procedures. Examples of passageway defects include tracheal defects, such as tracheomalacia, tracheobronchomalacia, tracheoesophageal fistula, tracheoinnominate fistula, congenital stenosis, acquired stricture, cancer (obstruction from tumors), idiopathic tracheomalacia or tracheal/airway reconstruction surgery. Other passageway defects include bronchomalacia and vein graft replacements, such as bypass obstructions in the arteries (coronary bypass) or weakened veins, arteries or capillaries. Example sources of external compression that can cause passageway defects include arteries, such as the pulmonary artery, the brachiocephalic artery, or the aorta, mechanical structures such as a tracheostomy tube or an arterial graft, scar tissue, edema and tumor. The implantable splinting device can also support luminal reconstruction with cartilage, bone, skin, mucosal and dermal grafts. In various embodiments, such an implantable splinting device is used as a result of surgical procedure, degenerative disease, trauma, or the like.

In various embodiments, the implantable splinting device of the present technology is formed of a material comprising a polymer, such as a biocompatible or biomedically acceptable polymer that may be biodegradable or non-biodegradable. The term "biodegradable" as used herein means that the implant comprising the polymer is slowly dissolved or disintegrated under physiological conditions in the human or other animal subject for a certain time and at some point only its degradation products are present in the body in a dissolved or comminuted form. At this point, solid components or fragments of the splinting either do not exist anymore or are so small as to be non-harmful or transported away by the subject's circulatory system. The degradation products should be substantially harmless in physiological terms and lead to molecules that either occur naturally in the human or other animal subject or can be excreted by the human or other animal subject.

The term "non-biodegradable polymer" as used herein means that the biomedically acceptable polymer forming the implant will not dissolve in the human or animal subject. These polymers do not substantially resorb, dissolve or otherwise degrade after implantation in a human or animal subject, under typical physiological conditions. In various embodiments, the implantable splinting device of the present technology comprises a polymer, such as a biodegradable polymer. Biodegradable polymers include polycaprolactone, polysebacic acid, poly(octaindiolcitrate), polydioxanone, polygluconate, poly(lactic acid) polyethylene oxide copolymer, modified cellulose, polyhydroxybutyrate, polyamino acids, polyphosphate ester, polyvalerolactone, poly-6-decalactone, polylactonic acid, polyglycolic acid, polylactides, polyglycolides, copolymers of the polylactides and polyglycolides, polye-caprolactone, polyhydroxybutyric acid, polyhydroxybutyrates, polyhydroxyvalerates, polyhydroxybutyrate-co-valerate, poly(1,4-dioxane-2,3one), poly(1,3-dioxane-2-one), poly-para-dioxanone, polyanhydrides, polymaleic acid anhydrides, polyhydroxy methacrylates, fibrin, polycyanoacrylate, polycaprolactone dimethylacrylates, poly-3-maleic acid, polycaprolactone butyl acrylates, multiblock polymers from oligocaprolactonediols and oligodioxanonediols, polyether ester multiblock polymers from PEG and poly(butlylene terephthalates), polypivotolactones, polyglycolic acid trimethyl carbonates, polycaprolactone glycolides, poly(methyl glutamate), poly (DTH-iminocarbonate), poly(DTE-co-DT-carbonate), poly(bisphenol A-iminocarbonate), polyorthoesters, polyglycolic acid trimethyl carbonate, polytrimethyl carbonates, polyiminocarbonates, poly(N-vinyl)-pyrrolidone, polyvinyl alcohols, polyester amides, glycolized polyesters, polypho sphoesters, polypho sphazenes, poly[p-(carboxyphenoxy) propane], polyhydroxy pentanoic acid, polyanhydrides, polyethylene oxide propylene oxide, and combinations thereof. In various embodiments, a preferred biodegradable polymer that forms the implantable splinting device comprises, or consists of, polycaprolactone.

In various embodiments, the implantable splinting device comprising the biodegradable polymer allows the passageway defect to heal naturally and then biodegrade or resorb in the subject. Having the implantable splinting device biodegrade eliminates need for a second surgery for removal of the implanted device and furthermore will not inhibit trachea regrowth in adults or growth in children. In various embodiments, the implantable splinting device is designed to have a degradation time that coincides with the healing time of the defect in the subject. "Degradation time" refers to the time for the implantable splinting device implanted to substantially and fully dissolve, disintegrate, or resorb.

Depending upon the subject and the time needed for recuperation and regeneration of the passageway, the degradation time may be about 3 weeks to about 60 months (5 years), or about 2 months to about 40 months (3.33 years), or about 6 months to about 36 months (3 years), or about 12 months to about 24 months (2 years). In certain embodiments, the preferred degradation time for an implantable splinting device according to the present technology is about 6 months to about 36 months (3 years). As noted above, in certain embodiments, a preferred biodegradable polymer used to form the implantable splinting device comprises polycaprolactone, which desirably enables such a degradation time of 6 months to about 36 months (3 years) under normal physiological conditions when implanted in an animal subject.

In certain embodiments, the implantable splinting device of the present technology optionally comprises a non-biodegradable polymer. The implantable splinting device may comprise multiple polymers, including one or more biodegradable polymers, one or more non-biodegradable polymers, and any combinations thereof. Suitable biomedically acceptable non-biodegradable polymers include polyaryl ether ketone (PAEK) polymers (such as polyetherketoneketone (PEKK), polyetheretherketone (PEEK), and polyetherketoneetherketoneketone (PEKEKK)), polyolefins (such as ultra-high molecular weight polyethylene, which may be crosslinked, and fluorinated polyolefins such as polytetrafluorethylene (PTFE)), polyesters, polyimides, polyamides, polyacrylates (such as polymethylmethacrylate (PMMA)), polyketones, polyetherimide, polysulfone, polyurethanes, and polyphenolsulfones.

The implantable splinting device of the present technology can further comprise one or more bioactive materials. Depending on such factors as the bioactive material, the structure of the implantable splinting device, and the intended use of the implantable splinting device, the bioactive material may be coated on a surface of the implantable splinting device, coated or otherwise infused in the pores or openings of the implantable splinting device, or mixed or compounded within the polymeric material of the implantable splinting device. Bioactive materials can include any natural, recombinant or synthetic compound or composition that provides a local or systemic therapeutic benefit. In various embodiments, the bioactive material promotes healing and growth of a collapsed trachea or a collapsed trachea with stenosis. Bioactive materials among those useful herein include cell adhesion factors, isolated tissue materials, growth factors, peptides and other cytokines and hormones, pharmaceutical actives, and combinations thereof. Cell adhesion factors include, for example, the RGD (Arg-Gly-Asp) sequence or the IKVAV (Ile-Lys-Val-Ala-Val) sequence. Isolated tissue materials include, for example, whole blood and blood fractions (such as red blood cells, white blood cells, platelet-rich plasma, and platelet-poor plasma), collagen, fibrin, acellularized dermis, isolated cells and cultured cells (such as hemopoietic stem cells, mesenchymal stem cells, endothelial progenitor cells, fibroblasts, reticulacytes, adipose cells, and endothelial cells). Growth factors and cytokines useful herein include transforming growth factor-beta (TGF-β), including the five different subtypes (TGF-β 1-5); bone morphogenetic factors (BMPs, such as BMP-2, BMP-2a, BMP-4, BMP-5, BMP-6, BMP-7 and BMP-8); platelet-derived growth factors (PDGFs); insulin-like growth factors (e.g., IGF I and II); fibroblast growth factors (FGFs), vascular endothelial growth factor (VEGF), epidermal growth factor (EGF) and combinations thereof. Examples of pharmaceutical actives include antimicrobials, antifungals, chemotherapeutic agents, and anti-inflammatories. Examples of antimicrobials include triclosan, sulfonamides, furans, macrolides, quinolones, tetracyclines, vancomycin, cephalosporins, rifampins, aminoglycosides (such as tobramycin and gentamicin), and mixtures thereof. In certain variations, an implantable splinting device comprises acellularized dermis, an acellularized tissue matrix, a composite of acellularized dermis matrix and designed polymer, and/or a composite of acellularized tissue matrix and designed polymer. In certain aspects, an implantable splinting device comprises an acellularized dermis layer disposed on one or more surfaces that will contact the passageway upon implantation.

Figure 1A:
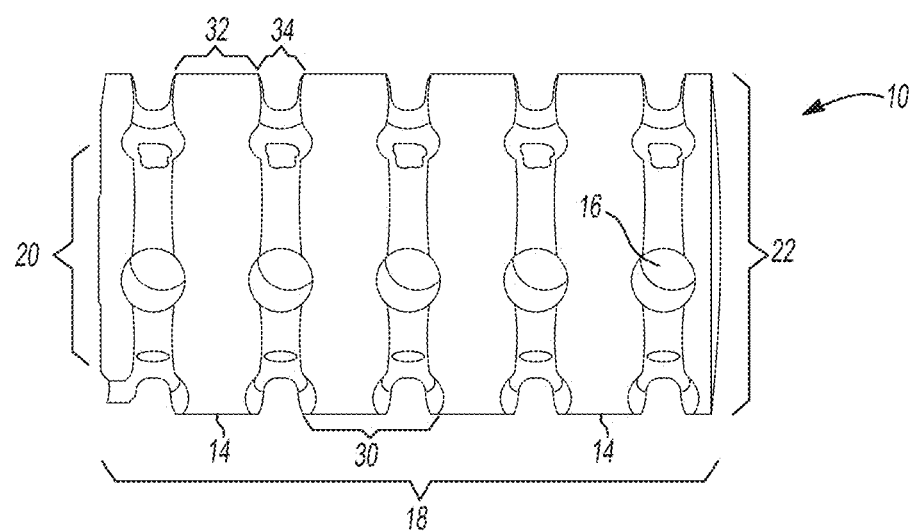
FIGS. 1A-1B show lateral (1A) and longitudinal (1B) perspective views of an implantable splinting device according to certain aspects of the present teachings.
Figure 1B:
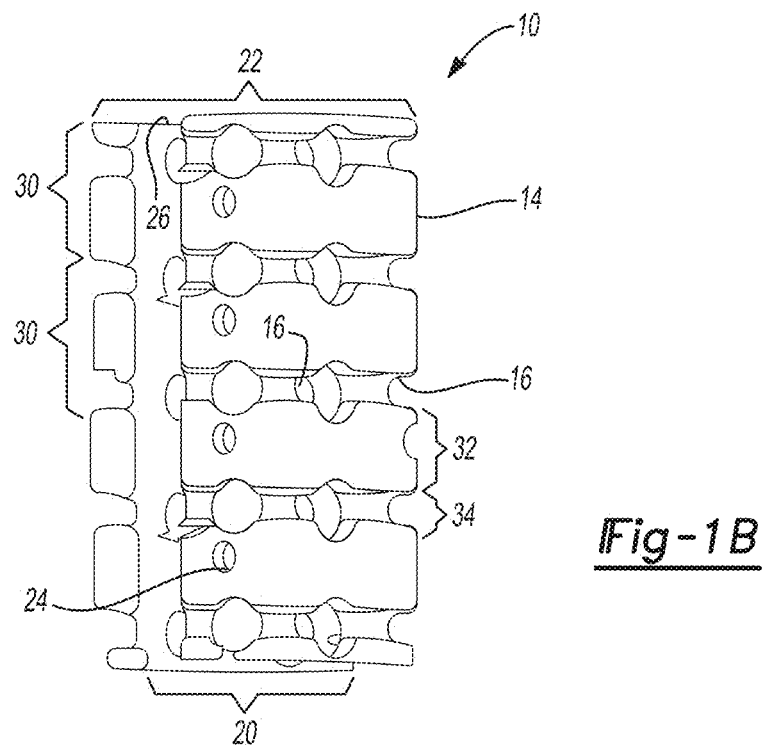

Referring to FIGS. 1A and 1B, the implantable splinting device 10 has a series of support structures 14 that are formed of a material comprising a biomedically acceptable polymer. The support structures 14 together define a structural component or body of the implantable splinting device 10. The structural component of implantable splinting device 10 has a cylindrical shape or an elongated "U-shape" capable of conforming to the physiological passageway to which it can be attached. In certain variations, the structural component of the implantable splinting device substantially conforms to the passageway, meaning that it has a shape the same as or similar to the passageway, so that it can provide adequate physical support when placed near or attached to the passageway. The present technology contemplates that the body or structural component of the implantable splinting device 10 may have other shapes, including partial cylindrical shapes that will be discussed below, which may only support or reinforce a portion of the circumference of the defective passageway. The implantable splinting device 10 further comprises a plurality of openings or apertures 16 defined in the support structures 14. As discussed above, the implantable splinting device 10 may be capable of being placed around a defective passageway in an animal subject, such as a trachea, a bronchi, an esophagus or a blood vessel of a subject. The structural component of the implantable splinting device 10 defines a length 18, an internal diameter 20, and an outer diameter 22. The support structures 14 formed of the polymeric material thus together extend along the implantable splinting device 10 to define the length 18 of the structural component body, as well as internal diameter 20 and outer diameter 22, which will be described in more detail below. The length 18 and outer diameter 22 can be designed from commonly used lengths or customized to a subject by using an image-based design approach specific to a human or animal subject.

The image-based design approach uses medical images or other data that is specific to the patient to customize the size of the implantable splinting device 10. The specific medical images and/or parameters are obtained from one or more imaging systems such as computed tomography (CT), a CT-fluoroscopy, fluoroscopy, magnetic resonance imaging (MRI), ultrasound, positron emission tomography (PET) and X-Ray systems or any other suitable imaging systems. The medical image data and/or parameters received from the imaging system provide a two-dimensional (2D), three-dimensional (3D) or four-dimensional (4D) model of an anatomical structure, organ, system or region of the patient. The image-based design of the 2D, 3D or 4D model may be created using MATLAB®, Mathematica®, or other CAD software design programs known in the art. For converting the design into a usable format for rapid prototyping and computer-aided manufacturing, a STL file format may be created. This file format is supported by many software packages such as Mimics® by Materialise, MATLAB®, IDL, and Amira®.

This 2D, 3D or 4D model of the implantable splinting device of the present technology may then be used to manufacture the implantable splinting device 10. The device made by a variety of suitable methods, including methods comprising solid free-form fabrication (SFF) techniques such as laser sintering, stereolithography, 3D printing and injection molding. In various embodiments, the preferred method is laser sintering. Laser sintering is a process involving the construction of a three-dimensional article by selectively projecting a laser beam having the desired energy onto a layer of particles. The laser sintering process can be paired with medical image data and/or parameters received from the imaging system for producing a customized implantable splinting device of the present technology.

In certain embodiments, the implantable splinting device 10 has a length 18 ranging from about 10 mm to about 60 mm. When the implantable splinting device 10 is used for a pediatric patient, the length 18 may range from about 10 mm to about 30 mm. When the implantable splinting device 10 is used for an adult patient, the length 18 may range from about 10 mm to about 60 mm.

Figure 2A:
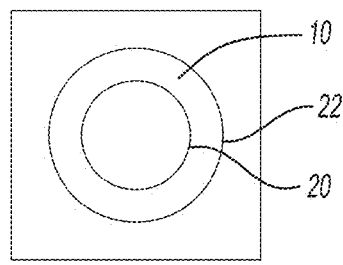
FIGS. 2A-2C show an in-plane lumen (2A), a square extrusion of a bellow wave (2B), and a triangle extrusion of a bellow wave (2C) according to certain aspects of the present teachings.

Referring to FIG. 1B and FIG. 2A, in various embodiments, the implantable splinting device 10 defines internal and outer diameters 20, 22 and has a cross-sectional shape that is a circular design (thus forming a cylindrically shaped body). The implantable splinting device 10 may also form a semi-circular, oval or semi-oval, or elliptical cross-sectional shape. In certain embodiments, the implantable splinting device 10 has an inner diameter 20 ranging from about 4 mm to about 30 mm and an outer diameter 22 ranging from about 5 mm to about 34 mm. When the implantable splinting device 10 is used for a pediatric patient, the inner diameter 20 may range from about 4 mm to about 12 mm and an outer diameter 22 ranges from about 5 mm to about 16 mm. When the implantable splinting device 10 is used for an adult patient, the inner diameter 20 may range from about 10 mm to about 30 mm and an outer diameter 22 may range from about 11 mm to about 34 mm.

Implantable splinting devices having bellow designs offer an advantage of being stiff under compression, but much more compliant in bending. In addition, the bellow in combination with an open tube design allows the implantable splinting device to open, thus allowing the passageway, such as a trachea, to grow. Referring to FIGS. 1A and 1B, the implantable splinting device 10 comprises a series of support structures 14, which can define a plurality of bellows 30 along length 18 so as to define a bellow configuration. The bellows 30 are defined by the support structures 14 and thus form a plurality of repeating protruding rings or regions 32 (which protrude in a radial direction and are farther from the center of the implantable splinting device 10 structure) corresponding to the outer diameter 22 interspersed with a plurality of recessed regions 34 (which are closer to the center of the implantable splinting device 10 structure in a radial direction) corresponding to the internal diameter 20 of the implantable splinting device 10. The protruding regions 32 and recessed regions 34 create a pleated bellow structure 30 along the length 18 of the implantable splinting device 10. A wave period of bellows 30 may be adjusted in the longitudinal and traverse directions to modify stiffness and compliance. The bellow wave period 30, including a single protruding bellow region 32 and a single recessed bellow region 34 may range from greater than or equal to about 1.5 mm to less than or equal to about 6 mm. The protruding bellow region 32 may have a length of greater than or equal to about 1 mm to less than or equal to about 4 mm. The period defined by recessed bellow regions 34 (between protruding bellow regions 32) may have a length ranging from greater than or equal to about 0.5 mm to less than or equal to about 2 mm.

The bellow 30 wave periods are designed from a bidirectional, Fourier series based bellow design approach. As one skilled in the art would appreciate, the functional bellow geometry can be changed in both the longitudinal and transverse directions to modify stiffness and compliance to create an axial rigid structure, but transversely compliant structure. This allows the implantable splinting device to have sufficient mechanical rigidity to prevent decompression of the passageway while being compliant in bending to allow flexing of the passageway.

Controlling implantable splinting device stiffness is an important factor in developing the optimal tracheal splint designs. Previously, there has been little ability to rigorously control splint design and then fabricate the splint to that specific design. Furthermore, because splints were typically made ad hoc from fixation plates, there was no ready method for scaling production. The inventive technology, on the other hand, enables a three-dimensional design and fabrication approach, which is a significant advance in the field, allowing controlled devices to be manufactured in scaled production.

An important consideration in designing an implantable splinting device is what mechanical properties are advantageous to optimally treat tracheomalacia, for example. A splint that is too stiff may erode the trachea and restrict tracheal growth, while a splint that is too compliant will not achieve the goal of maintaining tracheal patency. It is believed that in certain variations, an optimal bioresorbable implantable splinting device will restrict direct compression strains to less than or equal to about 10% (about 1 mm displacement) to maintain patency of a passageway, while permitting outward radial displacement 2-3 times the initial tracheal diameter under growth. It is theorized that such designs will maintain significantly larger passageway (e.g., tracheal) volume than no treatment. Accordingly, in certain variations, implantable splinting devices comprising bioresorbable polycaprolactone (PCL) for use as tracheal splints have mechanical properties, such that the implantable splinting device deforms less than or equal to about 1 mm under 50N of a compression load, but can deform to at least 1 to greater than or equal to 2 times an original diameter under 50N of radial pressure due to tissue growth forces (generated by the tissue growth in the passageway).

The implantable splinting device prepared in accordance with certain aspects of the present technology meets the following desirable criteria: 1) it is formed of a bioresorbable polymeric material, such as polycaprolactone, which maintains support for a predetermined duration (e.g., 24 months) but allows avoidance of an additional surgical procedure and anesthetic exposure for removal; 2) it predictably and effectively exerts a balanced radial force in the axial plane restoring and maintaining native lumen size of a passageway but is designed to allow for internal expansion facilitating growth; 3) it allows transverse plane movement and normal cervical range of motion; and 4) mucociliary architecture is unaltered by the external nature of the splint device.

In certain aspects, implantable splinting devices according to the present disclosure can be designed by using a custom MATLAB® program using Fourier series. In certain variations, the splinting device has a bellow design generated by such a custom-written MATLAB® software incorporating a Fourier series expansion. The image-design data generated by this software can then be imported into MIMICS™ to integrate holes for suturing to a passageway, like the trachea, within the splinting device and to size the device for a specific patient or subject. Design characteristics, including bellow wave geometry or shape (e.g., square wave, triangular wave, sine wave, cosine wave, and the like), bellow height, bellow wave period, a suture needle diameter, a suture needle spacing, an opening angle, a splint wall thickness, a splint internal diameter and splint length, which can be readily changed not only for customized patient reconstruction but for controlling the mechanical stiffness of the splint. All of these variables are incorporated in the image-based splint design according to certain aspects of the present teachings.

The bellow wave period shapes are created using a Fourier Series Expansion where the function is represented by the Fourier Series with a period 2*bellow wave length or 2*L:

$$\text{Approx: } f(x) = \frac{a_0}{2} + \sum_{n=1}^{\infty} \left( a_n \cos\frac{n\pi x}{l} + b_n \sin\frac{n\pi x}{l} \right)$$

The Fourier series coefficients are calculated from the following integral expressions:

$$a_0 = \frac{1}{2l}\int_{-l}^{l} f(x)dx; (n = 1, 2, \ldots)$$

$$a_n = \frac{1}{2l}\int_{-l}^{l} f(x)\cos\frac{n\pi x}{l}dx; (n = 1, 2, \ldots)$$

$$b_n = \frac{1}{2l}\int_{-l}^{l} f(x)\sin\frac{n\pi x}{l}dx; (n = 1, 2, \ldots)$$

Figure 2B:
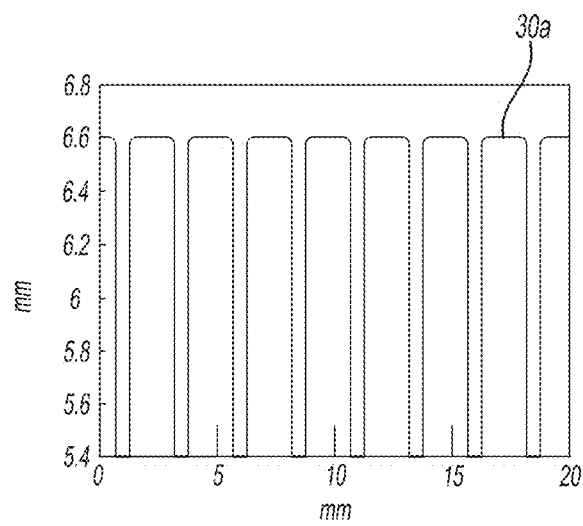

The outer diameter 22 in plane image (FIG. 2A) is perturbed in the longitudinal direction to follow the wave shape implemented through the Fourier expansion. The bellow wave periods 30 are adjusted in the longitudinal direction perpendicular to the outer diameter 22. Following extrusion of the bellow periods, an internal diameter 20 is implemented in the splinting device. In various embodiments, the bellows may define different shapes, like square, triangle, sine, cosine, and the like. FIG. 2B illustrates a square bellow wave 30a extrusion using the Fourier series and FIG. 2C illustrates a triangle bellow wave 30b extrusion using the Fourier series.

Using this program, bellow designs can be automatically generated with different wave shapes (for example, square versus triangular), different wave heights and periods, all of which can alter implantable splinting device mechanics. These designs can be imported into MIMICS™ anatomic CAD software to design surgical needle hole placement (FIG. 5B) and size the splint to a patient's or subject's trachea (see FIG. 13A). Finally, finite element analysis can be performed to simulate all designs under compression and growth forces to determine implantable splinting device mechanical performance. For an internal splint diameter of 7 mm, compressive displacements of less than 1 mm under 50N load can be maintained, while allowing between 6-21 mm (between 1 to 3 times initial diameter displacement) under 60N of radial growth pressure to achieve design objectives.

By using such techniques, in certain variations, up to 200 splints can be manufactured in a 4 to 5 hour period from bioresorbable polycaprolactone (PCL) polymer using a laser sintering process that allows building of splints of almost any three-dimensional (3D) anatomic complexity. This design/manufacturing capability allows splints to be designed and manufactured in a much more controlled manner and yet at much greater scale than any previous tracheal stent or implantable splint device.

Figure 2C:
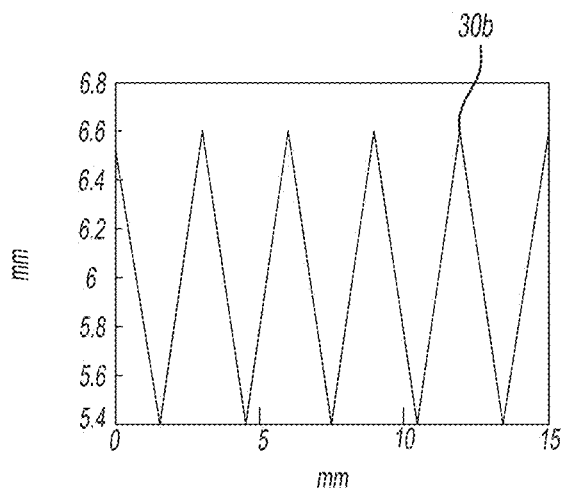

FIGS. 3A and 3B provide two alternative embodiments of three-dimensional bellow shapes for implantable splinting devices having the bellow configurations in FIGS. 2B and 2C. In FIG. 3A, the implantable splinting device 10a has a base design with the extrusion of a circular-shaped cross-section for a lumen with square wave shaped bellows 30a along a length 18a. Thus, a plurality of protruding bellow regions 32a are interspersed with recessed bellow regions 34a that together define orthogonal square-shaped bellows 30a along the length 18a of implantable splinting device 10a. In FIG. 3B, the implantable splinting device 10b instead has an extrusion of a circular cross-sectional lumen along the triangle wave 30b. Thus, the protruding bellow regions 32b are interspersed with recessed tapered bellow regions 34b that together define tapered triangular-shaped bellows 30b along a length 18b of implantable splinting device 10b.

With renewed reference to FIGS. 1A and 1B, an exemplary small pediatric implantable splinting device may have a length 18 of about 9.83 mm, a period or length of respective protruding bellow regions 32 is about 1.38 mm and the period or length of recessed regions 34 is about 0.85 mm (so that a period of an overall bellow 30 including a single protruding region 32 and a single recessed region 34 is about 2.23 mm). Further, certain apertures of the plurality of apertures 16 have a diameter of about 1.02 mm.

In another exemplary small pediatric implanting device, a length 18 is about 9.83 mm, a period or length of respective protruding bellow regions 32 is about 1.35 mm and the period or length of recessed regions 34 is about 0.69 mm (so that a period of an overall bellow 30 including a single protruding region 32 and a single recessed region 34 is about 2.04 mm). Further, certain apertures of the plurality of apertures 16 have a diameter of about 1.03 mm. Apertures 16 for receiving suture needles may have a smaller diameter of about 0.51 mm.

Figure 4:
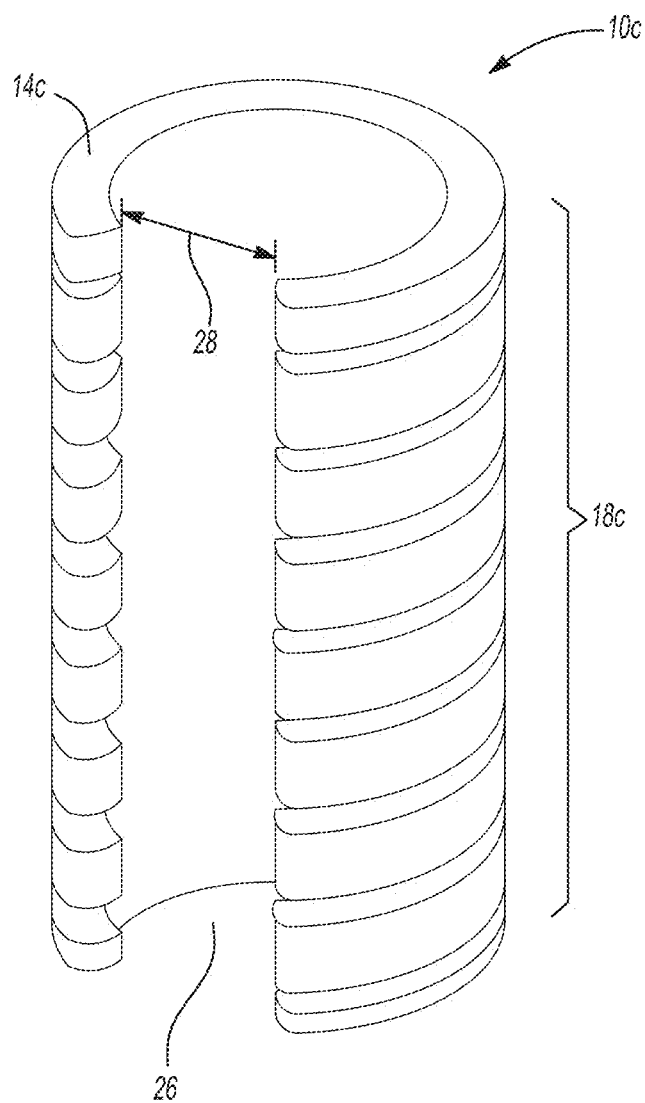
FIG. 4 shows a square wave bellow with a wedge cut opening for placement of an implantable splinting device around a passageway according to certain variations of the present teachings.

As discussed above, the implantable splinting devices (e.g., 10, 10a, 10b) are capable of being placed around a trachea, a bronchi, an esophagus and a blood vessel of a patient. In various embodiments, the implantable splinting device 10 optionally comprises a slit or longitudinal wedge 26 (see, e.g., FIG. 1B or 4). FIG. 4 shows a similar embodiment to that in FIG. 3A but with the longitudinal wedge 26 formed in an implantable splinting device 10c along a length 18c. The wedge 26 is cut into the implantable splinting device 10c to permit placement around the passageway, such as the trachea, the bronchi, the esophagus and the blood vessel of the subject or patient. A width 28 of the longitudinal wedge 26 may in certain variations range from about 4 mm to about 15 mm. As discussed below, the longitudinal wedge 26 may provide different opening widths 28 that correspond to different angles that desirably provide advantages during surgical procedures.

Figure 5A:
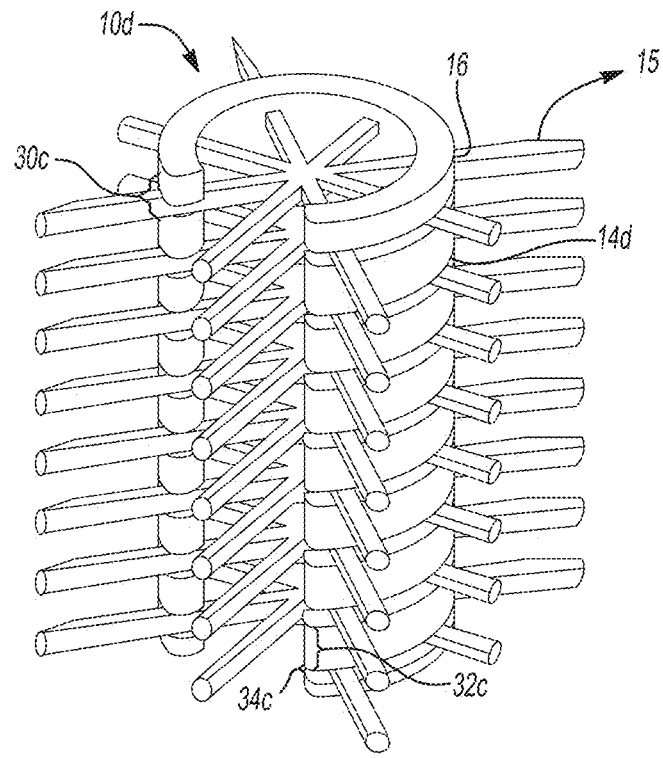
FIGS. 5A-5B show an implantable splinting device having a wedge and square bellow with a plurality of openings (5A) and a portion of the plurality of apertures configured to accept a suture needle (5B) according to certain aspects of the present teachings.

As shown in FIG. 1, the implantable splinting device 10 comprises a plurality of openings or apertures 16. Such apertures 16 may be pores, however, in preferred aspects are formed as larger macroscale apertures in the support structures 14. As one skilled in the art would appreciate, the apertures 16 allow for increased bending, flexibility of the implantable splinting device 10 and also for vascularization while the passageway defect is healing. The plurality of apertures 16 can be placed within the recessed regions (e.g., 34, 34a, 34b) of the bellow periods (e.g., 30, 30a, 30b). FIG. 5A provides an example of the plurality of apertures 16 created in an implantable splinting device 10d by a computer 3D image-based design by intersecting spokes 15 within the recessed bellow region periods 34c between the protruding bellow periods 32c that together define bellows 30c.

In various embodiments, the respective apertures 16 may have a diameter ranging from about 0.5 mm to about 3 mm. The apertures 16 are shown as being formed in each of the recessed bellow regions (e.g., 34, 34a, 34b, 34c); however, they may be selectively placed in only one recessed bellow region or selectively in certain predetermined recessed bellow regions (for example, in alternating recessed bellow regions 34, 34a, 34b, or 34c). Further, in alternative variations, apertures may be placed in other locations of the support structures 14, 14a, 14b, or 14c, such as in the protruding regions (e.g., 32, 32a, 32b, or 32c)

Figure 5B:
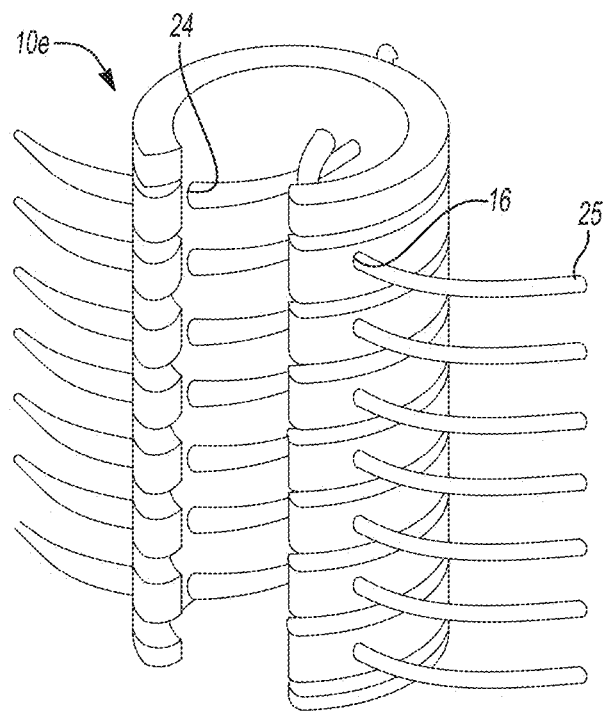

The apertures 16 of the implantable splinting devices (e.g., 10, 10a, 10b, 10c, or 10d) can be pre-aligned with holes to fit a surgical needle to allow for suturing to the affected passageway during surgery. Once the implantable splinting device (e.g., 10, 10a, 10b, 10c, or 10d) is placed around the passageway, such as the trachea, the bronchi, the esophagus and the blood vessel of the patient, the device is sutured to the area using a portion of a plurality of apertures 16 configured to accept the suture needle. FIG. 5B provides an example of a plurality of apertures 16 in an implantable splinting device 10e configured to accept a suture needle 24 created in the computer 3D image-based design by interposing surgical needle files 25 within the apertures 16 and through the aperture 16 configured to accept a suture needle 24. The aperture 16 configured to accept the suture needle 24 may have a diameter ranging from about 0.5 mm to about 3 mm.

Figure 11A:
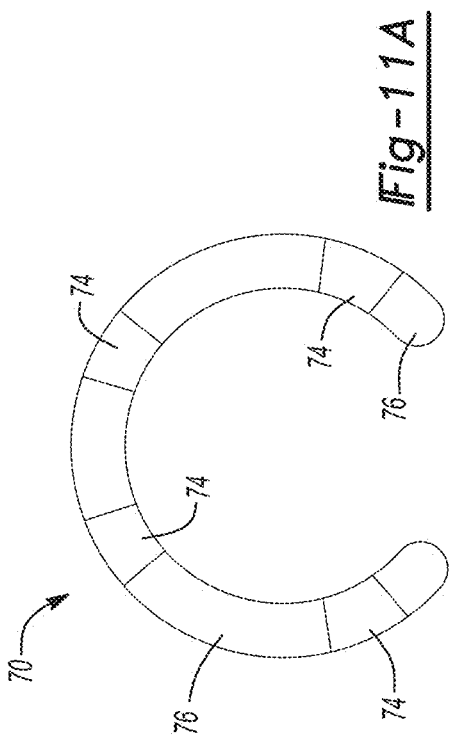
FIGS. 11A-11B show cross-sectional views of implantable splinting devices having differing radial patterns of apertures along a circumference capable of receiving sutures along the implantable splinting devices.
Figure 11B:
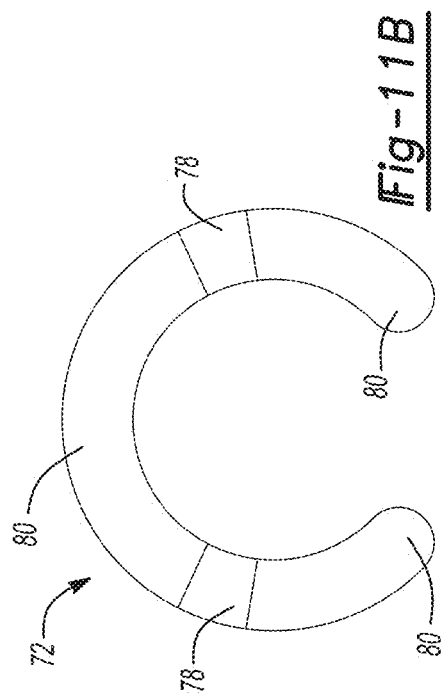

In FIGS. 11A and 11B, cross-sectional views of two different implantable splinting devices are shown. FIG. 11A shows a first implantable splinting device 70 and FIG. 11B shows a second implantable splinting device 72. The first implantable splinting device 70 comprises a plurality of apertures 74 (e.g., four apertures) disposed radially about the circumference of support sections 76. The plurality of apertures 74 are spaced for and capable of receiving suturing needles (not shown). The second implantable splinting device 72 comprises a plurality of apertures 78 (e.g., two apertures) disposed radially about a circumference defined by support sections 80. The plurality of apertures 78 are likewise spaced apart from one another for and capable of receiving suturing needles (not shown). Notably, having multiple apertures 74 radially disposed at different locations around the circumference of the implantable splinting device 70 may provide greater flexibility and ease of suturing during surgical implantation, as the physician or surgeon may select different openings for attaching sutures during the procedure. Notably, it is contemplated that implantable splinting devices according to certain aspects of the present teachings may have different numbers of apertures or openings for suturing to the defective passageway during implantation and having two or four apertures is non-limiting.

Figure 6A:
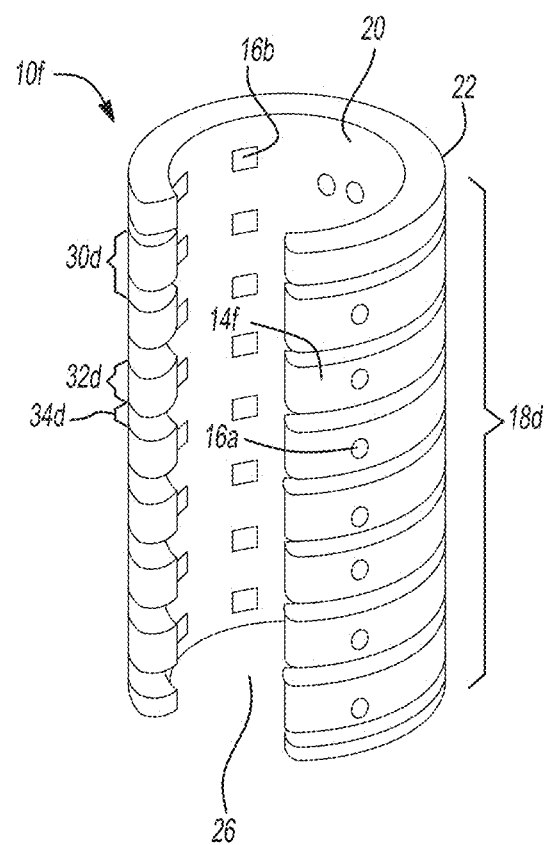
FIGS. 6A-6B show an implantable splinting device with a square wave bellow, a plurality of openings where a portion of the plurality of openings is configured to accept a suture needle, and a wedge removed from the splinting device according to certain aspects of the present teachings, shown in an isometric view (6A) a and lateral view (6B).
Figure 6B:
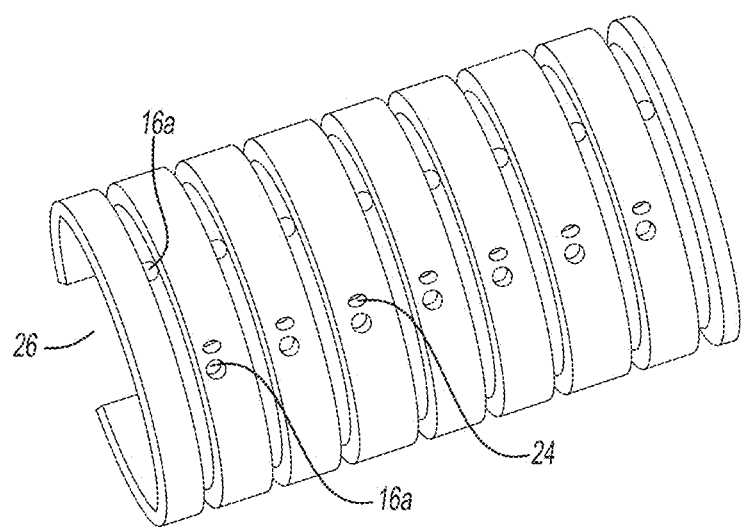

An exemplified 3D image-based design of the implantable splinting device 10f is illustrated in FIG. 6A comprising a first plurality of apertures 16a and a second plurality of apertures 16b. As shown in FIG. 6A, the apertures may have different shapes, which may be designed to provide different mechanical characteristics. By way of example, the first plurality of apertures 16a are circular and well-suited for receiving suturing needles, while the second plurality of apertures 16b have a rectangular shape to provide structural flexibility. Notably, other shapes are likewise contemplated, such as ovals, slits, squares, triangles, and the like. The plurality of apertures may have the same shape or may have a variety of distinct shapes as shown in the implantable splinting device 10f. The body of implantable splinting device 10f has a circular-shaped cross-section that forms a cylindrical shape with square wave shaped bellows 30d along a length 18d. Thus, a protruding bellow region 32d is interspersed with recessed bellow regions 34d that together define orthogonal square-shaped bellows 30d along the length 18d of implantable splinting device 10f. Further, implantable splinting device 10f has an opening wedge 26 to facilitate placement over a passageway. An exemplified 3D image-based design of FIG. 6B further illustrates the first plurality of pores 16a configured to accept a suture needle (not shown).

Figure 7A:
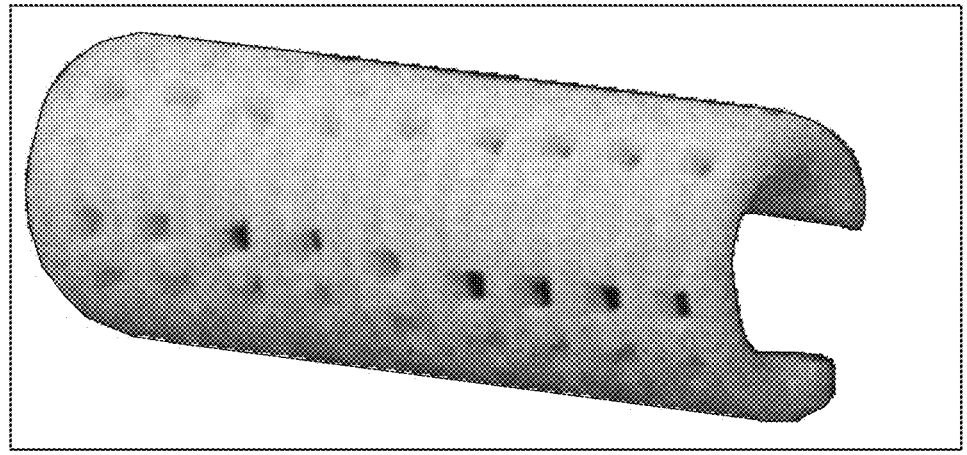
FIGS. 7A-7B show a tracheal splint device according to certain aspects of the present teachings made from a bioresorbable polycaprolactone polymer using laser sintering, shown in an anterior view (7A) and a posterior view (7B).
Figure 7B:
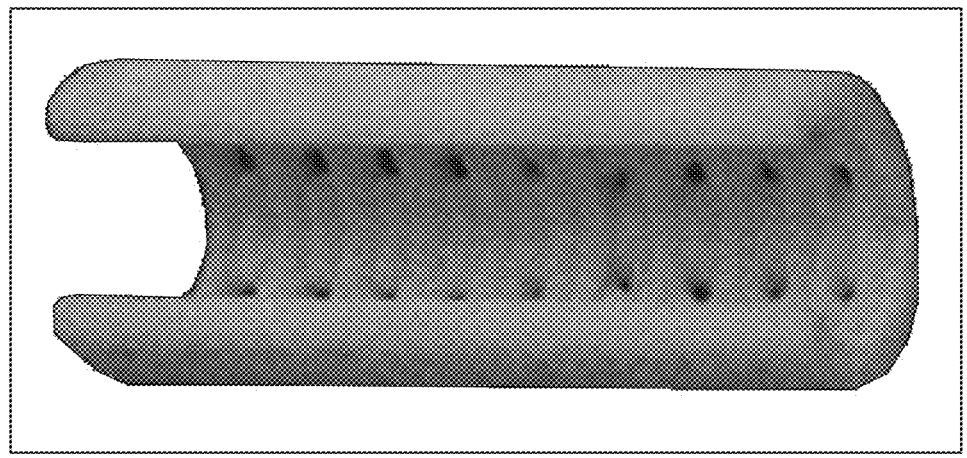

After undergoing modeling using the 3D image-based design, implantable splinting devices are made by a variety of suitable methods, including methods comprising solid free-form fabrication (SFF) techniques such as laser sintering, stereolithography, 3D printing and injection molding. FIGS. 7A and 7B illustrate a front and back view of an implantable bellowed tracheal splint device (like the design shown in FIGS. 6A-6B) made from the biodegradable polymer polycaprolactone using a laser sintering manufacturing process.

Figure 8:
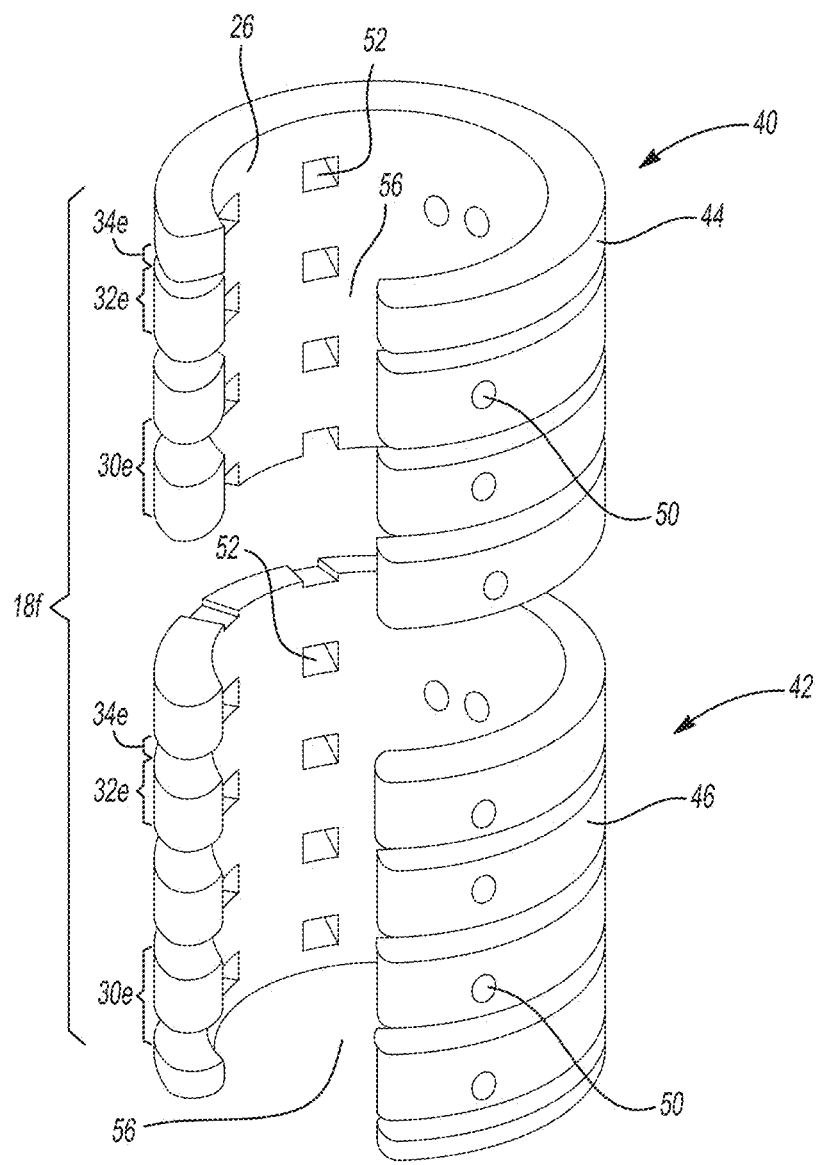
FIG. 8 shows a segmental implantable splinting device according to certain aspects of the present teachings.

While the implantable splinting device may be designed in one continuous segment, in certain embodiments, the implantable splinting device may comprise a first component and a second distinct component. Thus, such an implantable splinting device may comprise at least one segment capable of being placed around multiple portions of a passageway, such as a trachea, a bronchi, an esophagus and a blood vessel of a patient. This design also allows for increased growth while the passageway defect heals. As illustrated in FIG. 8, an implantable splinting device 10g is shown that includes a first segment 40 and a second distinct segment 42. The first segment 40 is formed of a first set of support structures 44 comprising a polymer, while the second segment 42 is formed of a second set of support structures 46 comprising a polymer. Each of the first and second segments 40, 42 comprises a first plurality of apertures 50 having a circular cross-sectional area for receiving a suture needle (not shown) and a second plurality of apertures 52 having a rectangular cross-sectional area to provide additional mechanical flexibility and openings for tissue growth. As shown, each of the first and second segments 40, 42 defines a series of bellow periods 30e, which includes a plurality of protruding bellow regions 32e interspersed with recessed bellow regions 34e that together define orthogonal square-shaped bellows 30e along the length 18f of implantable splinting device 10f. The first and second segments 40, 42 may have a length 18f ranging from about 4 mm to about 8 mm. Notably, the first segment 40 and the second segment 42 have substantially the same lengths as shown in FIG. 8; however, in alternative embodiments, the segments may respectively have different lengths, potentially different diameters, and different bellow periods or shapes. Furthermore, more than two segments are likewise contemplated. The first segment 40 and the second segment 42 of the implantable splinting device 10f also comprise a longitudinal wedge 56 that facilitates placement of the respective segments 40, 42 around a passageway.

Figure 9:
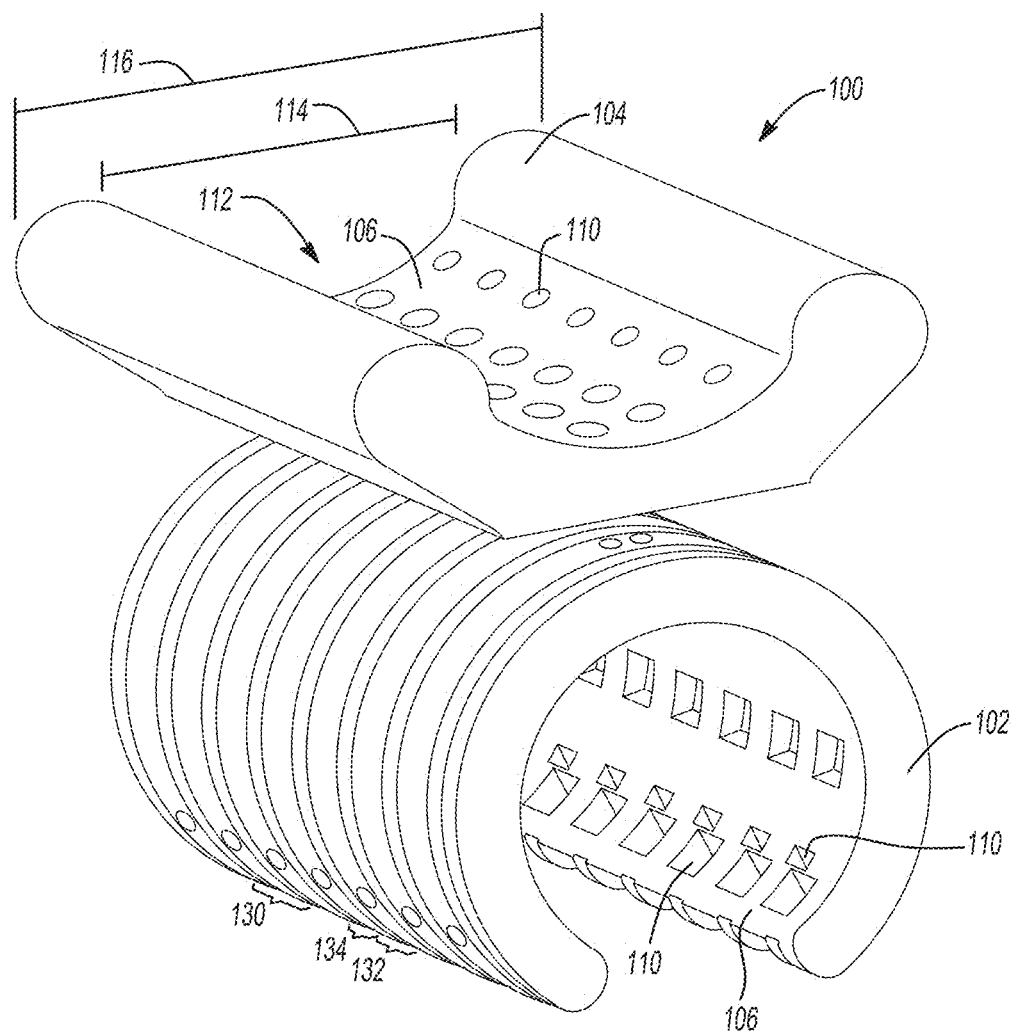
FIG. 9 shows an alternative embodiment of an implantable splinting device having an esophageal supporting section and a tracheal supporting section for use in treating tracheoesophageal fistulas.

In certain other embodiments, such as that shown in FIG. 9, an implantable splinting device 100 (shown as a cross-section) may placed between the trachea and the esophagus for treating tracheoesophageal fistulas. The implantable splinting device 100 for supporting a trachealesophageal fistula in a patient comprises a polymer material. The implantable splinting device 100 defines a first tracheal U-shaped structural component 102 and a second esophageal U-shaped structural component 104 that are defined by a series of support structures 106. Each of the first tracheal U-shaped structural component 102 and the second esophageal U-shaped structural component 104 comprises a plurality of apertures 110. In various embodiments, the implantable splinting device 100 comprising the first tracheal U-shaped structural component 102 and the esophageal U-shaped structural component 104 are designed to form a back to back single U-shaped structure to provide support to the trachea and the esophagus forming a device having an approximate H-shaped cross-section. In other embodiments, the implantable splinting device comprising a tracheal U-shaped structure and an esophageal U-shaped structure are implanted as separate components to provide support to the trachea and the esophagus. When using the implantable splinting device of such an embodiment to treat such conditions as tracheoesophageal fistulas, openings used 110 as suture holes may be absent where the first U-shaped tracheal structural component 102 and esophageal structural component 104 come into contact with each other.

The first tracheal U-shaped structural component 102 and the second esophageal U-shaped structural component 104 are designed and fabricated as described above. The second esophageal U-shaped structural component 104 has a flatter "U" shape and has a wider angle at the longitudinal opening or wedge 112. The second esophageal U-shaped structural component has an inner diameter or dimension 114 that may range from about 10 mm to about 40 mm and an outer diameter or dimension 116 ranging from about 12 mm to about 45 mm. The first tracheal U-shaped structural component 102 may have dimensions as discussed in any of the embodiments discussed above or herein. The openings of each respective U-shaped structural component allow for suturing each device to the trachea and esophagus of the patient.

In one exemplary embodiment, the first tracheal U-shaped structural component 102 and the esophageal U-shaped structural component 104 both have a length of about 18.82 mm. The first tracheal U-shaped structural component 102 has an inner diameter of about 10.43 mm. The bellows on the first tracheal U-shaped structural component 102 and the esophageal U-shaped structural component 104 may differ from one another or can be substantially the same, as shown in FIG. 9. For example, a period or length of respective protruding bellow regions 132 on the first tracheal U-shaped structural component 102 is about 1.38 mm and a period or length of recessed bellow regions 134 is about 1.16 mm (so that a period of an overall bellow 130 including a single protruding region 132 and a single recessed region 134 is about 2.54 mm). Apertures 110 for receiving suture needles on the first tracheal U-shaped structural component 102 may have a smaller diameter of about 0.72 mm. The second esophageal structural component 104 has an inner dimension 114 of about 5 mm.

FIGS. 18A-18C show another embodiment of an implantable splinting device 300 that comprises a first structural component 310 and a second distinct structural component 312. Each structural component 310, 312 comprises a plurality of rib support structures 314 and longitudinal support members 316. The first structural component 310 and the second structural component 312 together define different sides of a U-shaped structural component. The first structural component 310 has a plurality of receiving members 320 at a terminal edge 322 capable of receiving a plurality of connectors 330 on the second structural component 312. In this way, the connectors 330 can be connected or snapped into receiving members 320, so that the two structural components 310, 312 are joined together at an articulated joint or a hinge 340. One advantage of such a hinge design is that as a single structural component is formed by the joining of the first structural component 310 and the second structural component 312 (having a U-shaped structure), it cannot fold inwards, so that it maintains patency of a passageway, like a trachea. However, the hinge provides articulation or movement of each side outward, thus permitting a passageway to expand and grow (e.g., permitting a child's tracheal growth). Notably, other methods of connecting the first structural component 310 to the second structural component 312 to provide a clamshell movement known to those of skill in the art are likewise contemplated.

Figure 10C:
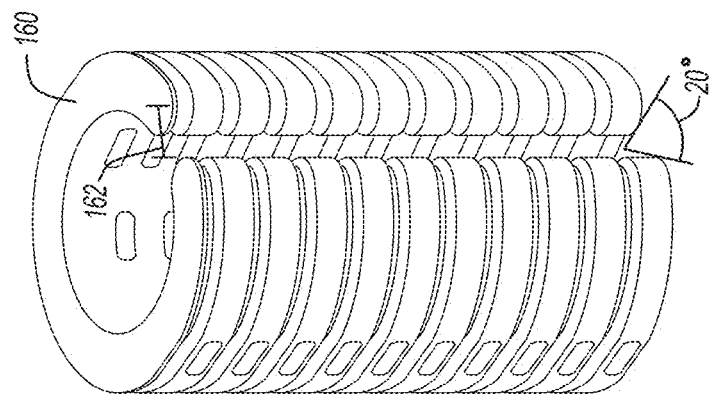
FIGS. 10A-10C show alternative embodiments of implantable splinting devices having different angles for longitudinal wedge openings, where FIG. 10A has a 120° opening angle, FIG. 10B has a 90° opening angle, and FIG. 10C has a 20° opening angle.
Figure 10B:
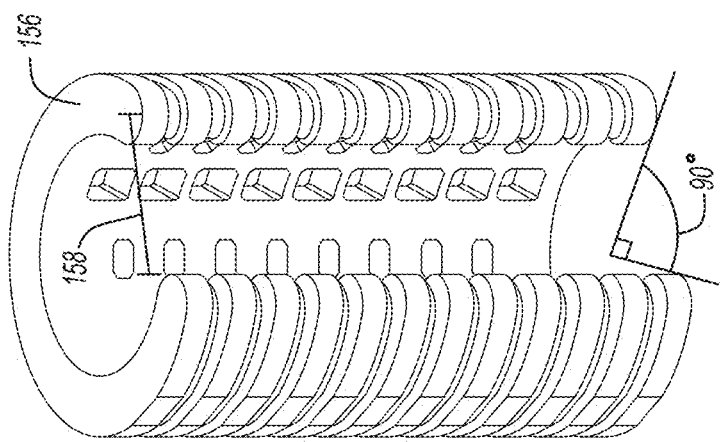
Figure 10A:
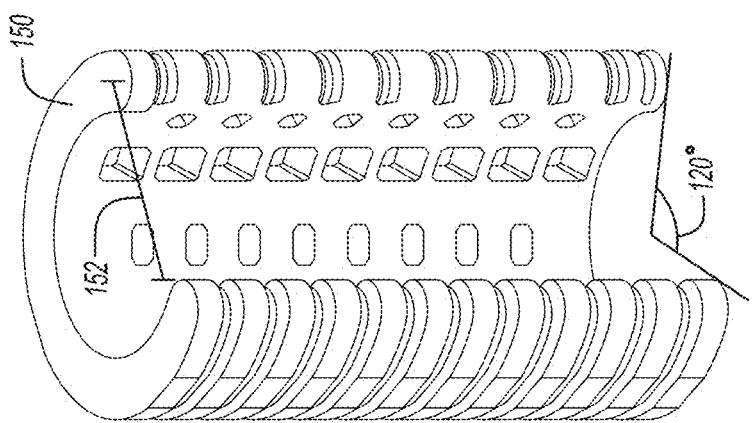

FIGS. 10A-10C show alternative embodiments of implantable splinting devices according to certain variations of the present disclosure, where each has a different opening angle for longitudinal wedge openings. In certain aspects, it is desirable to have an ability to select different opening angles for implantable splinting devices depending on the passageway to be supported, the subject in which the implantable splinting device is to be implanted, and surgical technique for implanting the devices. Thus, as shown in FIG. 10A, a first implantable splinting device 150 has a longitudinal wedge opening 152 with a relatively large opening angle of 120°. Comparatively, a second implantable splinting device 156 in FIG. 10B has a longitudinal wedge opening 158 and has a smaller opening angle of 90°. Finally, a third implantable splinting device 160 in FIG. 10C has a longitudinal wedge opening 162 with a relatively small opening angle of 20°. In certain aspects, a greater opening angle for a longitudinal wedge opening permits attaching the implantable splinting device to the passageway to provide anterior and posterior separation for the defective passageway, as the implantable splinting device is sutured to the defective passageway. Thus, depending upon the nature and extent of defect or collapse of the passageway, as well as the location and access to the passageway within the subject, it may be desirable to have differing opening angles for the implantable splint, which can be determined by the physician or when customizing the implantable splint device for a particular patient. In various aspects, an opening angle for a longitudinal opening along an implantable splinting device may range from greater than or equal to about 20° to less than or equal to about 270°.

Figure 12:
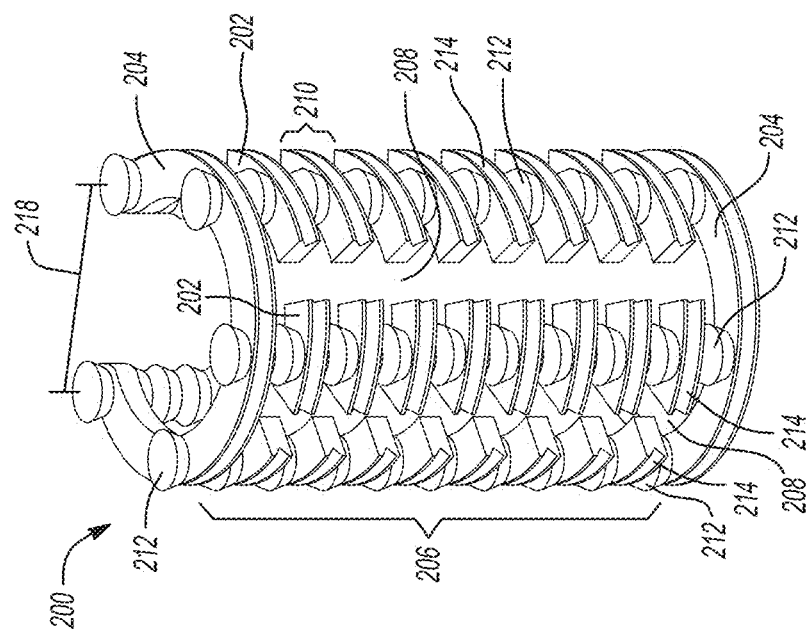
FIG. 12 shows an alternative embodiment of an implantable splinting device defining a plurality of support structures in the form of longitudinal ribs to provide open spaces for increased tissue growth and vascularization.

In FIG. 12, an alternative implantable splinting device 200 is shown. A plurality of support structures 202 defines two arcuate supports 204 of the implantable splinting device 200. The support structures 202 further define a plurality of longitudinal rib structures 206 each respectively attached to the terminal arcuate supports 204. The plurality of longitudinal rib structures 206 each define structural bellows 210 formed by a alternating pattern of discs 212 and arcuate plate shapes 214. Between each longitudinal rib structure 206 is an opening 208. Further, a longitudinal wedge opening 218 is formed along one side to permit placement of the implantable splinting device 200 over the defective passageway. The openings 208 serve both as locations for receiving sutures, but also to provide increased space for growth and vascularization of tissue of the passageway, such as tracheal growth and vascularization.

Tracheal splints may be designed with two different magnitudes of growth displacement ((a) 1 time initial implantable splinting device diameter and (b) greater than 2 times initial diameter of the implantable splinting device) while maintaining maximum displacements less than 1 mm under 50N compressive load (where the load is estimated based on maximum arterial pressure on the trachea). Bellow designs with two different wave shapes (square versus triangle) and four different wave heights (0, 1, 2, and 3 mm) are generated using the MATLAB® design program described above. All designs are imported into MIMICS™ to verify splint geometry fits a subject's target passageway dimensions from CT scans. Needle holes are introduced into each design using the suturing needle .STL files. Finite element models are created for each design to determine compressive displacement, bending displacement and growth displacement. Designs which meet criteria for experimental Group 1 (high growth stiffness=displacement of 1× initial splint diameter and less than 1 mm compressive displacement under 50N load) and Group 2 (low growth stiffness=displacement greater than 2× initial splint diameter and less than 1 mm compressive displacement under 50N load) are selected for fabrication and testing.

Tracheal splints are fabricated using an EOS Formiga 100 laser sintering machine. Polycaprolactone (PCL) is purchased as pellets and milled to a mean particle size of about 100 micrometers. A fabrication run uses 1 kg of PCL to build 150-200 splints. Sample splints from each build are micro-CT scanned to verify manufactured splints match original design using MIMICS™. If more than one design meets the criteria for an experimental group, the design with the largest opening displacement within the group limits is chosen.

Fabricated implantable splinting devices are tested in uniaxial compression perpendicular to the long axis of the implantable splinting device. An MTS Alliance RT/30 electromechanical test frame is run under 1 mm/min displacement control. Load and displacement values are recorded and analyzed using TestWorks™ Software. Stiffness of the constructs can be calculated from a linear region on the load versus displacement curve. For growth stiffness and displacement, splints are opened using a balloon catheter inflated to a pressure of 380 mmHg (50 N) controlled by a manometer. The unloaded and loaded deformation states are documented using a GE Locus micro-computed tomography scanner (having a scan resolution of 27 µm) and the relative compliance of the splints can be assessed by measuring the splint opening distance.

Example 1

This example investigates a slowly degrading, bioresorbable tracheobronchial splint placed extralumenally to address severe pediatric tracheomalacia. Evaluation of an external novel 3D printed bioresorbable airway splint prepared in accordance with certain aspects of the present technology is conducted for severe, life-threatening tracheobronchomalacia in a porcine animal model. Infant Yorkshire pigs are selected as a preclinical model because the porcine trachea has similar biomechanical and anatomic properties to the growing human trachea. Three control animals (n=3) undergoing tracheal cartilage division and inner tracheal lumen dissociation and three experimental animals (n=3) receiving the same model with overlying placement of the newly developed airway splint are evaluated.

Institutional Animal Care and Use Committee (IACUC) approval was obtained at the University of Illinois. Two-month-old Yorkshire pigs (n=6) are randomly assigned to treatment (n=3) or control groups (n=3). One pig was excluded secondary to an intraoperative emesis and aspiration event.

The novel implantable tracheobronchial splinting device is designed to treat airway malacia at the tracheal and/or bronchial level. The implantable splinting device has an open cylindrical bellow design with periodically spaced pores to allow suturing of the trachea within the splint. See FIGS. 14A-14C. As discussed above, the implantable splinting device is automatically generated using a custom written MATLAB™ program that allows the user to specify splint diameter, length, opening angle, suture pore spacing and bellow wave period, height and shape. Finite element analysis of compression, 3-point bending, and internal growth is performed on initial designs. The design is generated as image data and directly converted to a surface representation in .STL format as input data for manufacturing. The splint is manufactured from polycaprolactone (PCL) using laser sintering (EOS P 100 Formiga system), a 3D printing technology, that has been adapted to utilize PCL to build complex 3D structures. Prior to surgical implantation, all scaffolds are ethylene oxide sterilized and allowed to outgas.

FIGS. 14A-14B respectively show a posterior view and oblique view of an implantable splinting device 230 having a longitudinal opening 232 with a 90° opening angle. The predesigned plurality of openings 234 for needle hole placement are shown in FIG. 14B. FIG. 14C shows a laser sintered polycaprolactone implantable splinting device formed from the designs of FIGS. 14A and 14B. Polycaprolactone scaffolds forming the implantable splinting device are customized to fit porcine trachea from animals weighing approximately 20 kg.

Each pig underwent surgical creation of a model for tracheomalacia described in FIGS. 15A-15E. Intravenous ketamine, tiletamine/zolazepam, xylazine and atropine, followed by inhaled isoflurane 3-5% are used for anesthetic. The volume of the anesthetic mixture is 0.1 ml/kg or 2 ml for 20 kg. Body temperature, heart rate and breathing rate as well the palpebral reflex are used to assure the appropriate depth of anesthesia.

The cervical skin is prepped and draped in sterile fashion. An anterior cervical approach via a vertical, midline skin incision over the larynx and trachea is performed. The sternothyroid and sternohyoid musculature, thyroid, and cervical thymus were dissected and retracted laterally, providing wide exposure to the trachea. FIG. 15A shows an illustration of an exposed trachea 250 having a plurality of cartilaginous rings 252. A malacic segment 260 was produced by extraluminal resection of tracheal ring 3 (262) followed by subperichondrial dissection of the next four consecutive tracheal rings 252, as shown in FIG. 15B. To ensure near complete or complete dynamic collapse, lateral dissection of the internal mucosal shown at 266 was carried posterolateral and inferior allowing near complete dissociation from external tracheal layers and preventing maintenance of patency. See FIG. 15C. Care was taken to avoid endoluminal tears, though if encountered, a single, interrupted 4-0 vicryl was used for repair. With the internal mucosa protected, the overlying tracheal rings are sharply divided creating four inferiorly based, distinct, narrow strips. FIGS. 15D and 16A show the inferiorly based tracheal cartilage 270 with intervening outer mucosa 272. The surgical sites of the three control animals were then closed.

In the experimental group, after creating the tracheomalacia model as in the control animals, each experimental animal had a 14 mm internal diameter PCL implantable splinting device placed. The internal mucosa 270, or surgically created malacic segment, was suspended to the external PCL airway implantable splinting device 272 using 4-0 vicryl or prolene sutures 274 passed through prefabricated and designed needle holes in the splint. As shown in FIGS. 15E and 16B, four sutures 274 at the superior and inferior lateral aspects of the airway 250 are placed, with additional sutures placed as necessary. The malacic trachea is then suspended as the sutures are sequentially tied. The surgical sites of the three control animals were then closed. Antibiotic therapy, ceftiofur 5.0 mg/kg, was administered intraoperatively.

Post-operatively, temperature, appetite, behavior and tenderness at the incision/implant sites were monitored. Furthermore, the validated Westley Croup Scale was used for daily clinical assessments of the animals (Table 1).

TABLE 1

Animal Daily Clinical Scoring System based on the Westley Clinical Croup scale.

| Subcostal Retractions | |
|---|---|
| None | 0 |
| Mild | 1 |
| Moderate | 2 |
| Severe | 3 |
| Stridor | |
| None | 0 |
| With agitation | 1 |
| At rest | 2 |
| Cyanosis | |
| None | 0 |
| With agitation | 4 |
| At rest | 5 |
| Level of consciousness | |
| Normal | 0 |
| Disoriented | 5 |
| Air entry | |
| Normal | 0 |
| Decreased | 1 |
| Markedly decreased | 2 |

Scores for the control group were not included as survival duration did not extend beyond the first post-operative day. Overnight mortality was assigned a time of death of 23:59 pm. To determine whether the differences seen between the two groups were statistically significant, a nonpaired, two-tailed Student t test was performed. Differences that showed a P value less than 0.05 were considered significant.

Pig mean weight was 21 kg with a range of 16 kg to 25 kg. No animals exhibited respiratory symptoms prior to surgery (Westley Score of 0). Complete or near complete inner lumen collapse was confirmed in all 6 pigs, which was accompanied by severe inspiratory stridor in all cases. There were no intraoperative deaths or complications.

All three control pigs displayed severe stridor, cyanosis, and retractions post-operatively. Decision to euthanize was made when level of consciousness changes were displayed. Daily post-operative clinical score using the Westley Scale are reported in FIG. 17. The animal with the longest survival, into post-operative day 7, received the splint and had a Westley clinical score rising from 3, peaking at 11, and stabilizing in the moderate range. The two additional animals receiving the implantable splinting device died between post-operative days 3 and 4 with minimal clinical signs of respiratory distress. Eventual mortality in each animal was attributed to infection in airway proximity.

Overall duration of survival is detailed for each animal in Table 2.

TABLE 2

Duration of survival in animals with a model of severe tracheomalacia with and without an interventional airway splint. (+, statistically significant p = 0.0495)

| | Weight (kg) | Survival (h:mm:ss) | p value |
|---|---|---|---|
| Control | | | |
| Animal 1 | 16.3 | 3:00:00 | |
| Animal 2 | 25.4 | 20:39:00 | |
| Animal 3 | 24.3 | 1:00:00 | |
| Splint | | | |
| Animal 4 | 21.3 | 84:14:00 | |
| Animal 5 | 20.0 | 167:09:00 | |
| Animal 6 | 20.0 | 86:29:00 | 0.0495 |

In the control group, times to death for the three animals were 1 hour, 3 hours, and 20 hours and 39 minutes. In the group receiving the implantable splinting device, time to death was significantly longer than that in the control group (p=0.0495 by signed rank-sum test) at 84 hours and 14 minutes, 86 hours and 29 minutes, and 167 hours and 9 minutes.

The severity of our tracheomalacia model in this experiment allowed for the assessment of airway splint efficacy in survival. Infection secondary to intraluminal needle hole communications was likely responsible for the pigs receiving the implantable splinting devices passing. It is notable that two of the three experimental animals had been clinically appearing excellent (Westley score of 1 and 2) prior to death. A modification to our model maintained an anterior island of full thickness trachea including cartilage, allowing for avoidance of mucosal needle holes, though still with extensive posterolateral mucosal dissection and near complete collapse. This animal had witnessed cardiopulmonary arrest post-operatively and was emergently returned to the operating room for implantable splinting device placement. Approximately 8 weeks post-operative, there continues to be no sign of infection and the animal has maintained excellent clinical appearance.

Example 2

In this example, a customized, bioresorbable tracheal implantable splinting device according to certain aspects of the present teachings is successfully implanted into a human subject. The implantable splinting device is used to treat tracheobronchomalacia (TBM), which presents with dynamic airway collapse and respiratory insufficiency and in the past has been difficult to treat.

The patient was born at 35 weeks gestation without respiratory distress. At six weeks of age, he exhibited chest wall retractions and difficulty feeding; by two months of age, his symptoms progressed, requiring endotracheal intubation. An extensive medical diagnostic work-up revealed anomalous origin and malposition of the pulmonary arteries, with criss-cross anatomy, right pulmonary hypoplasia and compression of the left mainstem bronchus between an abnormally leftward-coursing ascending aorta and an anteriorly displaced descending aorta (tethered by a short ligamentum arteriosum), air trapping and post-obstructive pneumonia. Despite creation of a tracheostomy and placement of tracheostomy tube, periodic respiratory arrests occurred.

Institutional Review Board approval for Emergency FDA Device Use and informed consent were obtained to use a custom designed and fabricated resorbable, tracheal implantable splinting device, prepared in accordance with the inventive technology. The implantable splinting device was computationally designed from the patient's computed tomographic image and fabricated via laser-based 3D-printing, to treat the patient's imminently life-threatening TBM.

A bellows topology was employed, similar to a vacuum cleaner hose, to provide resistance against collapse while simultaneously allowing flexion, extension, and expansion with growth. The design was imported into MIMICS™ software (Materialise) and manufactured with polycaprolactone (PCL), using laser sintering on an EOS Formiga P100 system.

FIGS. 13A-13B show models of an implantable splinting device used for treating a tracheobronchomalacia condition according to certain aspects of the present technology. FIG. 13A shows a model of a trachea and bronchi from the patient. The defective malacic segment is circled. The implantable splinting device formed from 3D laser sintering that comprises polycaprolactone is shown in the inset. FIG. 13B shows the implantable splinting device applied to the bronchus of the model to support the malacic segment.

After transposition of the right pulmonary artery and failed aortopexy, sutures were placed around the circumference of the malacic left bronchus and tied through interstices of the implantable splinting device, expanding the patient's bronchus. FIG. 13C shows surgical implantation of the implantable splinting device in the three-month old human patient. The splinting device is placed around the left bronchus, which is then sutured into the implantable splinting device to open the obstructed bronchus.

Subsequent bronchoscopy revealed normal patency of the bronchus without dynamic collapse. The previously static, hyperinflated left lung immediately demonstrated ventilatory variation in size. The partial pressure of carbon dioxide in venous blood decreased from 88 to 48 mmHg. By 21 days after the procedure, the patient was removed from ventilator support and was discharged home with the tracheostomy in place. Four months after surgery, bronchoscopy demonstrated a patent left main bronchus. Full resorption of the implanted splinting device is estimated to take 3 years.

The implantable splinting device of various aspects of the present teachings are designed to provide sufficient rigidity to maintain airway patency, while allowing internal expansion necessary for tracheal growth. Combining high resolution imaging, computational design, CAD and 3D biomaterial printing enables the creation of such novel implantable devices expeditiously for conditions that are anatomically specific for a given patient. The laser sintering manufacturing process is able to rapidly fabricate splints with a defined external shape, internal pore size and architecture.

The bioresorbable nature of the implantable splinting device allows for growth of the native trachea while avoiding additional surgical and anesthetic exposures. The biomaterial used to construct the implantable splinting device according to certain preferred embodiments, polycaprolactone, is specifically chosen for its maintenance of structural integrity for greater than 24 months in human clinical trials to date. This duration ideally matches the time generally required for growth and development of the trachea sufficient for resolution of symptoms in tracheomalacia. Furthermore, PCL material induces a lower inflammatory response than certain other biomedically acceptable polymers, such as PLGA, as demonstrated by lower MHC-II and GFAP expression. Accordingly, the present teachings provide a novel and unique bioresorbable external implantable splinting device that is designed to ameliorate severe, life-threatening pediatric tracheomalacia and other similar conditions.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

In other variations, an implantable splinting device for supporting a defect in a passageway of human or animal subject comprises one or more support structures together defining a structural component that substantially conforms to at least a portion of the passageway. The one or more support structures comprise a biomedically acceptable polymeric material. Further, the one or more support structures may optionally comprise a longitudinal opening formed within the one or more support structures to facilitate placement of the implantable splinting device over the passageway. The implantable splinting device comprises a plurality of apertures defined in at least a portion of the one or more support structures, which are capable of receiving a suture for attaching the implantable splinting device to at least a portion of the passageway.

In certain variations, the implantable splinting device is designed for placement around at least a portion of a passageway selected from the group consisting of: a trachea, a bronchi, an esophagus, and a blood vessel. The passageway defect may be selected from the group consisting of: tracheomalacia, tracheoesophageal fistula tracheoinnominate fistula, congenital stenosis, acquired stricture, cancer (obstruction from tumors), idiopathic tracheomalacia, tracheal/airway reconstruction surgery, bronchomalacia, weakened veins and a coronary bypass.

In certain variations, the implantable splinting device may comprise one or more support structures that together define a structural component that has an inner diameter and an outer diameter. The inner diameter optionally ranges from greater than or equal to about 4 mm to less than or equal to about 30 mm and the outer diameter optionally ranges from greater than or equal to about 5 mm to less than or equal to about 34 mm. The implantable splinting device optionally has a length ranging from greater than or equal to about 10 mm to less than or equal to about 60 mm.

In certain aspects, the polymer that forms the implantable splinting device comprises a biodegradable polymer. The biodegradable polymer is optionally polycaprolactone, in certain embodiments. The biodegradable polymer may have a degradation time of from about 10 months to about 24 months. In other aspects, the polymer comprises a non-biodegradable polymer. The implantable splinting device optionally further comprises a bioactive agent, wherein the bioactive agent is selected from the group consisting of: a cell adhesion factor, an isolated tissue material, a growth factor, a peptide, a cytokine, a hormone, a pharmaceutical active, and combinations thereof. In certain variations, the implantable splinting device comprises acellularized dermis. In certain preferred aspects, a shape of the structural component defined by the one or more support structures is a bellow configuration. Thus, the one or more structural components comprise a plurality of bellows. Each bellow of the plurality of bellows can have a wave period of greater than or equal to about 1.5 to less than or equal to about 6 mm. Each bellow of the plurality of bellows comprises a protruding region (in a radial direction) and a recessed region (in a radial direction). In certain variations, a length of the protruding region is greater than or equal to about 1 mm to less than or equal to about 4 mm. In certain variations, a length of the recessed region of the bellow is greater than or equal to about 0.5 mm to less than or equal to about 2 mm.

In other aspects, a width of the longitudinal opening ranges from greater than or equal to about 4 mm to less than or equal to about 15 mm. In certain aspects, a plurality of apertures respectively has a diameter ranging from about 0.5 mm to about 3 mm. In other variations, the implantable splinting device comprises a first structural component and a second structural component. The first structural component is a tracheal U-shaped structure and a second structural component is an esophageal U-shaped structure.

In other aspects, the present technology provides an implantable splinting device for supporting a defect in a passageway of a human or animal subject that comprises one or more support structures together defining a body or structural component that substantially conforms to at least a portion of the passageway. The implantable device comprises a plurality of apertures defined in at least a portion of the one or more support structures. The one or more support structures comprise a biomedically acceptable polymeric material, so that the body or structural component is capable of restricting displacement to less than 10% under a direct compression load of about 50N, while permitting outward radial displacement of at least 100% of an initial diameter of the body or structural component under non-stress conditions under a radial pressure of about 50N. The biodegradable polymer may be polycaprolactone and the biodegradable polymer can optionally have a degradation time of from about 10 months to about 24 months. In certain aspects, the implantable splinting device is designed from a set of medical image data specific to the patient.

In other aspects, the present technology provides an implantable splinting device for supporting a trachealesophageal fistula in a patient comprising a polymer. The implantable splinting device may comprise a tracheal U-shaped structural component and an esophageal U-shaped structural component. The structural components may be formed from a series of support structures and comprise a plurality of apertures.

The present technology additionally provides a method of making an implantable splinting device for application to a passageway defect in a patient comprising: providing a polymer, forming the polymer into a U-shaped structure, forming a series of support structures in the U-shaped structure, and integrating a plurality of pores within the series of support structures.

An advantageous feature of the present technology is a unique implantable splinting device that can be designed from the standard diameters and lengths of the trachea, bronchi, esophagus and blood vessels or customarily designed from the patient's specific medical image data prior to surgery.

In other aspects, the present technology may provide a method of making an implantable splinting device for application to a passageway defect in a patient, where a polymer is formed into a U-shaped structure having a series of support structures; and a plurality of apertures are integrated into the series of support structures. In certain aspects, the implantable splinting device is configured for being placed around a trachea, a bronchi, an esophagus and a blood vessel of a patient. In other aspects, the implantable splinting device is designed from a set of medical image data specific to the patient.

In other variations, a method of making an implantable splinting device for application to a passageway defect in a patient comprises designing a structural component for the implantable splinting device from a set of medical image data of the passageway defect specific to the patient. Then, a biodegradable polymer is laser sintered to form a structural component that substantially conforms to the designed structural component. Lastly, a plurality of pores is integrated within the structure capable of receiving a suture for attaching the implantable splinting device to at least a portion of the passageway. In certain variations, the implantable splinting device is configured for being placed around at least a portion of a passageway of the patient selected from the group consisting of: a trachea, a bronchi, an esophagus and a blood vessel. In certain aspects, the biodegradable polymer is optionally polycaprolactone and has a degradation time of from about 10 months to about 24 months.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

What is claimed is:

1. An implantable splinting device for supporting a defect in a passageway of a human or other animal subject comprising:
   one or more bellow support structures formed of a biocompatible polymeric material and together defining a structural component that substantially conforms to at least a portion of the passageway,
   a longitudinal opening formed within the one or more bellow support structures to facilitate placement of the implantable splinting device over the passageway; and
   a plurality of apertures defined in at least a portion of the one or more bellow support structures, the plurality of apertures capable of receiving a suture for attaching the implantable splinting device to at least a portion of the passageway,
   wherein each of the one or more bellow support structures comprises:
   a protruding region having a radially outermost surface that extends parallel to a longitudinal axis of the implantable splinting device, extends circumferentially from a first side of the longitudinal opening to a second side of the longitudinal opening, and defines a first diameter, and
   a recessed region defining a second diameter, wherein the second diameter is less than the first diameter.

2. The implantable splinting device of claim 1, wherein the implantable splinting device is designed for placement around and substantially conforms to at least a portion of the passageway selected from the group consisting of: a trachea, a bronchi, an esophagus, and a blood vessel.

3. The implantable splinting device of claim 1, wherein the defect in the passageway is selected from the group consisting of: tracheomalacia, tracheoesophageal fistula, tracheoinnominate fistula, congenital stenosis, acquired stricture, cancer (obstruction from tumors), idiopathic tracheomalacia, tracheal/airway reconstruction surgery, bronchomalacia, weakened veins and a coronary bypass.

4. The implantable splinting device of claim 1, wherein the structural component has an inner diameter and an outer diameter, wherein the inner diameter ranges from greater than or equal to about 4 mm to less than or equal to about 30 mm and the outer diameter ranges from greater than or equal to about 5 mm to less than or equal to about 34 mm, and wherein the implantable splinting device has a length ranging from greater than or equal to about 10 mm to less than or equal to about 60 mm.

5. The implantable splinting device of claim 1, wherein the biocompatible polymeric material comprises a biodegradable polymer having a degradation time from about 10 months to about 24 months.

6. The implantable splinting device of claim 5, wherein the biodegradable polymer is polycaprolactone.

7. The implantable splinting device of claim 1, wherein the structural component is capable of restricting displacement to less than 10% under a direct compression load of about 50 newtons (N), while permitting outward radial displacement of at least 100% of an initial diameter of the structural component under non-stress conditions under a radial pressure of about 50 newtons (N).

8. The implantable splinting device of claim 1, wherein the implantable splinting device further comprises a bioactive agent, wherein the bioactive agent is selected from the group consisting of: a cell adhesion factor, an isolated tissue material, a growth factor, a peptide, a cytokine, a hormone, a pharmaceutically active compound, and combinations thereof.

9. The implantable splinting device of claim 8, wherein the implantable splinting device comprises acellularized dermis, an acellularized tissue matrix, a composite of acellularized dermis matrix and polymer, or a composite of acellularized tissue matrix and polymer.

10. The implantable splinting device of claim 1, wherein a wave period of the one or more bellow support structures is greater than or equal to about 1.5 mm to less than or equal to about 6 mm.

11. The implantable splinting device of claim 1, wherein a first length of the protruding region is greater than or equal to about 1 mm to less than or equal to about 4 mm and a second length of the recessed region is greater than or equal to about 0.5 mm to less than or equal to about 2 mm.

12. The implantable splinting device of claim 1, wherein a width of the longitudinal opening ranges from greater than or equal to about 4 mm to less than or equal to about 15 mm.

13. The implantable splinting device of claim 1, wherein the plurality of apertures respectively has a diameter ranging from about 0.5 mm to about 3 mm.

14. The implantable splinting device of claim 1, wherein the implantable splinting device comprises a first structural component and a second structural component.

15. The implantable splinting device of claim 1, wherein the radially outermost surface of the protruding region has a first length of greater than or equal to about 1 mm and the recessed region defines a second length of greater than or equal to about 0.5 mm.

16. The implantable splinting device of claim 1, wherein the radially outermost surface of the protruding region of each bellow support structure has a length of greater than or equal to about 1 mm to less than or equal to about 4 mm.

17. The implantable splinting device of claim 1, wherein the recessed region is radially recessed in all locations relative to the protruding region.

18. The implantable splinting device of claim 1, wherein the recessed region extends circumferentially from the first side of the longitudinal opening to the second side of the longitudinal opening.

19. A method of making an implantable splinting device for application to a passageway defect in a human or other animal subject comprising:

laser sintering or three-dimensional (3D) printing a biocompatible polymeric material to form a structural component comprising one or more bellow support structures that substantially conforms to a portion of a passageway having the passageway defect specific to the human or other animal subject, wherein the structural component comprises a longitudinal opening formed within the one or more bellow support structures to facilitate placement over the passageway, and where each of the one or more bellow support structures is formed of a biocompatible polymeric material and comprises:

a protruding region extending circumferentially from a first side of the longitudinal opening to a second side of the longitudinal opening and having a radially outermost surface that extends parallel to a longitudinal axis of the implantable splinting device and defines a first diameter;

a recessed region defining a second diameter, wherein the second diameter is less than the first diameter; and integrating a plurality of pores within the structural component capable of receiving a suture for attaching the implantable splinting device to at least a portion of the passageway.

20. The method of claim 19, further comprising designing a structural component for the implantable splinting device from a set of medical image data of the passageway defect specific to the human or other animal subject prior to the laser sintering or three-dimensional (3D) printing.

21. The method of claim 19, wherein the implantable splinting device is configured for placement around at least a portion of the passageway of the subject selected from the group consisting of: a trachea, a bronchi, an esophagus and a blood vessel.

22. The method of claim 19, wherein the biocompatible polymeric material is polycaprolactone and has a degradation time of from about 10 months to about 24 months.

* * * * *